United States Patent
Fadli et al.

(10) Patent No.: US 7,892,294 B2
(45) Date of Patent: Feb. 22, 2011

(54) METHOD FOR DYEING KERATIN FIBERS USING AT LEAST ONE COMPOUND OF AZOMETHINE TYPE COMPRISING A PYRAZOLOPYRIDINE UNIT

(75) Inventors: Aziz Fadli, Chelles (FR); Stéphane Blais, Palaiseau (FR)

(73) Assignee: L'oreal S.A. (FR)

( * ) Notice: Subject to any disclaimer, the term of this patent is extended or adjusted under 35 U.S.C. 154(b) by 0 days.

(21) Appl. No.: 12/769,140

(22) Filed: Apr. 28, 2010

(65) Prior Publication Data
US 2010/0275389 A1   Nov. 4, 2010

Related U.S. Application Data

(60) Provisional application No. 61/177,740, filed on May 13, 2009.

(30) Foreign Application Priority Data
Apr. 30, 2009   (FR) .................... 09 52895

(51) Int. Cl.
  *A61Q 5/10*   (2006.01)
  *C07D 231/44*   (2006.01)

(52) U.S. Cl. ............. 8/405; 8/406; 8/435; 8/570; 8/572; 8/573; 8/576; 548/367.7; 132/202; 132/208

(58) Field of Classification Search ............. 8/405, 8/406, 435, 570, 572, 573, 576; 132/202, 132/208; 548/367.7
See application file for complete search history.

(56) References Cited

U.S. PATENT DOCUMENTS

| | | | |
|---|---|---|---|
| 5,445,943 A | 8/1995 | Hoenes | |
| 5,525,480 A | 6/1996 | Zimmermann et al. | |
| 7,288,124 B2 | 10/2007 | Fadli | |
| 7,582,123 B2 | 9/2009 | Fadli et al. | |
| 2009/0044348 A1 * | 2/2009 | Fadli et al. ............ | 8/405 |

FOREIGN PATENT DOCUMENTS

| DE | 39 42 355 A1 | 6/1991 |
|---|---|---|
| DE | 43 11 460 A1 | 10/1994 |
| EP | 1 634 574 A2 | 3/2006 |
| EP | 2 011 787 A1 | 1/2009 |

OTHER PUBLICATIONS

French Search Report for FR 0952895, dated Jan. 8, 2010.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

Provided herein is a method for dyeing keratin fibers, comprising applying to the keratin fibers, at least one composition comprising at least one compound chosen from compounds of leuco type of formula (I), dyes of azomethine type containing a pyrazolopyridine unit of formula (II) corresponding to the compounds of formula (I), mesomeric forms, isomers and tautomers thereof, and also acid-addition salts thereof and solvates thereof:

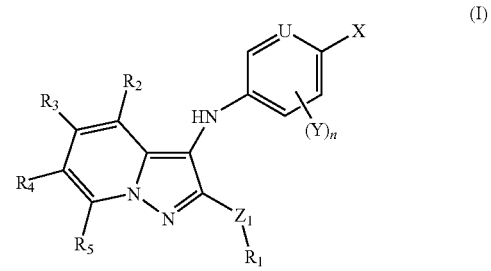

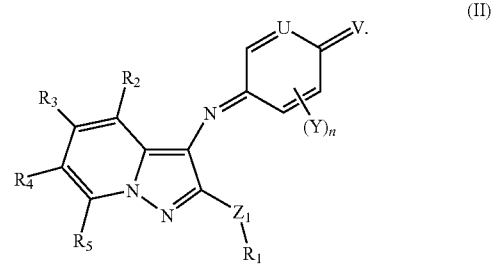

15 Claims, No Drawings

METHOD FOR DYEING KERATIN FIBERS USING AT LEAST ONE COMPOUND OF AZOMETHINE TYPE COMPRISING A PYRAZOLOPYRIDINE UNIT

This application claims benefit of U.S. Provisional Application No. 61/177,740, filed May 13, 2009. This application also claims benefit of priority under 35 U.S.C. §119 to French Patent Application No. 0952895, filed Apr. 30, 2009.

Disclosed herein is a method for dyeing keratin fibers, and for example human keratin fibers such as the hair, using at least one compound of azomethine type comprising a pyrazolopyridine unit.

It may be known to dye keratin fibers with dye compositions comprising direct dyes. These compounds can be colored and coloring molecules that may have affinity for the fibers. It may be known practice, for example, to use direct dyes of the nitrobenzene type, anthraquinone dyes, nitropyridine dyes, and dyes of the azo, xanthine, acridine, azine or triarylmethane type.

These dyes can be applied to the fibers, optionally in the presence of at least one oxidizing agent, if it is desired to obtain a simultaneous lightening effect on the fibers. Once the leave-on time has passed, the fibers can be rinsed, and optionally washed and dried.

The colorations resulting from the use of direct dyes are colorations that may often be chromatic, but can be, however, temporary or semi-permanent since the nature of the interactions that bind the direct dyes to the keratin fiber, and their desorption from the surface and/or the core of the fiber, may be responsible for their poor dyeing power and their poor relative fastness with respect to washing or perspiration. These direct dyes can be also generally light-sensitive since the resistance of the chromophore to photochemical attack can be poor, which may lead to fading of the hair coloration over time. The sensitivity of these dyes to light may depend on their distribution uniformly or as aggregates in and/or on the keratin fiber.

To obtain similar results, it can be also possible to use the uncolored, reduced form of these dyes and to apply it to the fibers in the presence of at least one oxidizing agent so as to generate the colored and coloring oxidized form. The coloration obtained may then be eliminated and then reformed rapidly by passing from one form to the other.

Thus, it can be known from French patent application FR 2 917 737 to use compounds of azomethine type comprising a pyrazolinone unit and reduced forms thereof so as to obtain a keratin fiber coloration that can be eliminated and then reformed easily.

Provided herein are novel direct dyes for reversibly dyeing keratin fibers, while at the same time giving good dyeing properties.

For example, one aspect of the present disclosure is to provide direct dyes for obtaining a strong, chromatic, aesthetic, sparingly selective coloration in varied shades, which may withstand the various attacking factors to which the hair may be subjected, such as shampoos, light, sweat and permanent reshaping, and which can be removed easily.

Also disclosed herein is a method for dyeing keratin fibers comprising applying to the keratin fibers at least one composition comprising at least one compound chosen from leuco form compounds of formula (I), dyes of azomethine type comprising a pyrazolopyridine unit of formula (II), mesomeric forms, isomers and tautomers thereof, and also acid-addition salts thereof and solvates thereof:

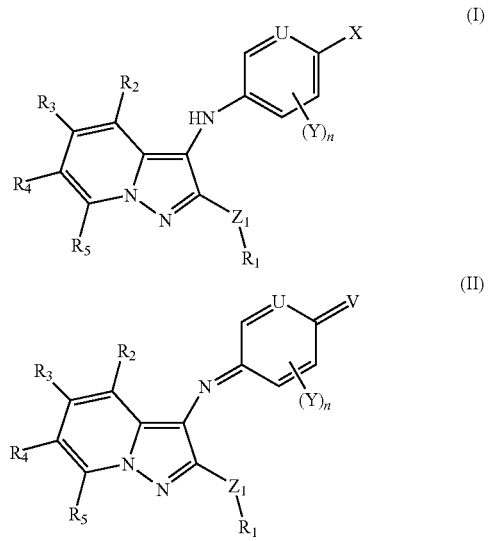

in which:

$Z_1$ represents an oxygen atom, or a group $NR_6$, when $Z_1$ represents $NR_6$ then $R_1$ and $R_6$ can form, together with the nitrogen atom to which they are attached, a saturated, unsaturated or aromatic, optionally substituted 5- to 8-membered heterocycle, $Z_1$ can also represent a divalent radical S, SO or $SO_2$ when $R_1$ is a methyl, $R_1$ and $R_6$ independently represent:
a hydrogen atom,
an optionally substituted $C_1$-$C_{10}$ alkyl radical, wherein the substituent can be a saturated, unsaturated or aromatic, optionally substituted 5- to 8-membered (hetero)cycle, or
a saturated, unsaturated or aromatic, optionally substituted 5- to 8-membered (hetero)cycle, $R_2$, $R_3$, $R_4$ and $R_5$ independently represent:
a hydrogen atom,
an optionally substituted $C_1$-$C_4$ alkyl,
a group chosen from $NH_2$, $NHR_{10}$, $NR_{11}R_{12}$, OH and $OR_9$, wherein $R_9$ and $R_{10}$ independently represent a linear or branched, optionally substituted $C_1$-$C_6$ alkyl, $R_{11}$ and $R_{12}$, which may be identical or different, represent an optionally substituted linear or branched $C_1$-$C_6$ alkyl, or $R_{11}$ and $R_{12}$, together with the nitrogen atom to which they are attached, form a saturated, unsaturated or aromatic 5- to 8-membered heterocycle optionally comprising at least one other radical chosen from N, O, S, $SO_2$ and CO, wherein the heterocycle is optionally substituted, or two adjacent $R_2$, $R_3$, $R_4$ and $R_5$, together with the two carbon atoms to which they are attached, form a saturated or unsaturated, optionally substituted (hetero)cycle;

n is an integer ranging from 0 to 3;
U represents CR or N;
R represents
a hydrogen atom,
a $C_1$-$C_4$ alkyl optionally substituted with a hydroxyl;
a $C_1$-$C_4$ alkoxy optionally substituted with a hydroxyl; or
a (di)($C_1$-$C_4$)alkylamino in which the alkyl part is optionally substituted with a hydroxyl;

X represents:
a hydroxyl;
a group $NR'_1R''_1$, wherein $R'_1$ and $R''_1$ are independently chosen from a hydrogen atom; a $C_1-C_6$ alkyl radical optionally substituted with at least one radical chosen from a hydroxyl, $(C_1-C_2)$alkoxy, amino, and $(di)(C_1-C_2)$alkylamino; a phenyl optionally substituted with at least one radical chosen from hydroxyl, amino, and $(C_1-C_2)$alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from oxygen and nitrogen atoms, and optionally substituted with at least one radical chosen from halogen atoms, aminos, $(di)(C_1-C_4)$alkylamino, hydroxyl, carboxyl, carboxamido, $(C_1-C_2)$alkoxy, and $C_1-C_4$ alkyl radicals, optionally substituted with at least one radical chosen from hydroxyl, amino, (di)alkylamino, alkoxy, carboxyl, and sulfonyl;

when X represents a group $NHR'_1$ and when U represents a group CR in which R denotes an alkoxy, then X and U together can form a 6-membered ring of morpholine type, optionally substituted with at least one $C_1-C_4$ alkyl;

V represents
an oxygen atom;
a group $NR'_1$, wherein $R'_1$ is chosen from a hydrogen atom; a $C_1-C_6$ alkyl optionally substituted with at least one radical chosen from hydroxyl, $(C_1-C_2)$alkoxy, amino and $(di)(C_1-C_2)$alkylamino; a phenyl radical optionally substituted with at least one radical chosen from hydroxyl, amino and $(C_1-C_2)$alkoxy;

when V represents a group $NR'_1$ and when U represents a group CR in which R denotes an alkoxy, then V and U may form a 6-membered ring of morpholine type, optionally substituted with at least one $C_1-C_4$ alkyl;

Y, which may be identical or different, represent:
a hydroxyl;
a $C_1-C_4$ alkyl;
a $C_1-C_4$ hydroxyalkyl;
a halogen atom;
an oxygen atom substituted with a radical chosen from a $C_1-C_4$ alkyl, an aryl and a heteroaryl, these radicals optionally substituted with at least one hydroxyl; or
a group $NR'_2R'_3$;

$R'_2$ and $R'_3$, which may be identical or different, are chosen from
a hydrogen atom;
a $C_1-C_4$ alkylcarbonyl optionally substituted with a quaternary ammonium group, or with a cationic or non-cationic nitrogenous heterocycle optionally substituted with at least one $C_1-C_4$ alkyl;
an aminocarbonyl;
a $C_1-C_6$ alkyl optionally substituted with at least one radical chosen from hydroxyl, $(C_1-C_2)$alkoxy, amino, and $(di)(C_1-C_2)$alkylamino; and
a phenyl radical optionally substituted with at least one radical chosen from hydroxyl, amino, and $(C_1-C_2)$alkoxy radicals; or $R'_2$ and $R'_3$ form, together with the nitrogen atom to which they are attached, a saturated or unsaturated, 5- to 7-membered heterocycle optionally comprising at least one additional heteroatom chosen from oxygen and nitrogen atom, and optionally substituted with at least one radical chosen from halogen atoms and amino, $(di)(C_1-C_4)$alkylamino, hydroxyl, carboxyl, (di)alkylcarboxamido, $(C_1-C_2)$alkoxy, and $C_1-C_4$ alkyl, optionally substituted with at least one radical chosen from hydroxyl, amino, (di)alkylamino, alkoxy, carboxyl, and sulfonyl; or two radicals Y borne by two adjacent carbon atoms form, together with the carbon atoms to which they are attached, a saturated or unsaturated, aromatic or non-aromatic, 5- to 6-membered cyclic or heterocyclic group optionally substituted with at least one $C_1-C_4$ alkyl.

Provided herein is also at least one novel compound chosen from the leuco form compounds of formula (I), the dyes of azomethine type comprising a pyrazolopyridine unit of formula (II), mesomeric forms, isomers and tautomers thereof, the acid-addition salts thereof and the solvates thereof.

Provided herein is also a composition for dyeing keratin fibers, comprising, in a suitable dyeing medium, at least one compound chosen from the leuco form compounds of formula (I), the dyes of azomethine type comprising a pyrazolopyridine unit of formula (II), the mesomeric forms, isomers and tautomers thereof, acid-addition salts thereof and the solvates thereof.

Provided herein is a multi-compartment device for performing the method for dyeing keratin fibers in accordance with the disclosure.

Unless otherwise indicated, the limits of the ranges of values that are given in the context of the disclosure are included in these ranges.

In the context of the disclosure, unless otherwise mentioned, the term "alkyl" means linear or branched alkyl radicals, which may be substituted or unsubstituted. Unless specifically listed, they may be substituted with any conventional substituent in the field of dyeing that does not change the dyeing properties of the compounds of formula (I) and/or (II).

An alkoxy is an alkyl-O-radical, the alkyl being as defined previously.

A (di)alkylamino is an amino radical that may be substituted with one or two alkyl radical.

A (di)alkylcarboxamido is a carboxamido radical that may be substituted with at least one alkyl.

Similarly, when the (hetero)cyclic defined for formula (I) and/or (II) are substituted, they may be substituted with any conventional radical in the field of dyeing that does not change the dyeing properties of the compounds of formula (I) and/or (II). As examples of substituents on these rings or heterocycles, mention may be made of alkyl, substituted alkyl, hydroxyl, alkoxy, amino, alkylamino, dialkylamino, thio, alkylthio, carboxyl, alkylcarbonyl, sulfonyl, amido, etc.

The nitrogenous heterocycle formed by $R_1$ and $R_6$ may comprise at least one additional heteroatom, for example, at least one heteroatom chosen from N, O, S, SO, $SO_2$ and —CO—. It may also be optionally substituted, for example as described above.

In formulae (I) and (II) above, when $R_1$ and/or $R_6$ represents a substituted alkyl, the substituents are for example chosen from halogens, radicals —OH, —$OR_9$, —$NH_2$, —$NHR_{10}$, —$NR_{11}R_{12}$, —$COR_{13}$, —O—CO—$R_{13}$, —CO—$OR_{14}$, —$NR_{15}$—CO—$R_{16}$, —CO—$NR_{15}R_{16}$ and —$SO_3H$, saturated or unsaturated cyclic radicals optionally comprising at least one heteroatom chosen from N, S and O, the ring itself being optionally substituted; $R_9$, $R_{10}$, $R_{11}$ and $R_{12}$, which may be identical or different, are as defined previously; $R_{13}$, $R_{14}$, $R_{15}$ and $R_{16}$, which may be identical or different, represent a hydrogen or a $C_1-C_6$alkyl. In formulae (I) and (II) above, when $R_1$ and/or $R_6$ represents a substituted alkyl, the substituents can be also chosen from radicals —$OSO_2R$, R representing a linear or branched $C_1-C_4$ alkyl or an optionally substituted aromatic radical. Examples that may be mentioned include the radicals —OH, —$OR_9$, —$NH_2$, —$NHR_{10}$, —$NR_{11}R_{12}$ and —$COR_{13}$, and cyclic radicals such as imidazole, piperazine, pyrrolidine, pyridine, piperidine, morpholine or pyrimidine.

According to at least one embodiment of the disclosure, the compounds of formula (I) or (II) above are such that $Z_1$ represents an oxygen atom, a radical $NR_6$ or a radical $NR_6$ forming with $R_1$ a heterocycle.

The radical $R_6$ may be chosen from a hydrogen atom, a $C_1$-$C_6$ alkyl; a $C_1$-$C_6$ alkyl substituted with at least one radical chosen from a hydroxyl, an amino, a ($C_1$-$C_4$)alkylamino, and a di($C_1$-$C_4$)alkylamino; and a $C_1$-$C_6$ alkyl substituted with a nitrogenous heterocycle, for example piperazinyl, imidazolyl, pyrrolidinyl, pyridyl, morpholinyl or piperidyl.

According to at least one embodiment, $Z_1$ can represent an oxygen atom or an NH.

According to the disclosure, $R_1$ may be chosen from a $C_1$-$C_6$ alkyl, a $C_1$-$C_6$ alkyl substituted with at least one hydroxyl, a $C_1$-$C_6$ alkyl substituted with at least one amino or at least one (di)($C_1$-$C_4$)alkylamino, a $C_1$-$C_6$ alkyl substituted with at least one nitrogenous heterocycle, for example piperazinyl, imidazolyl, pyrrolidinyl, pyridyl, morpholinyl, or piperidyl. For example, $R_1$ is chosen from a $C_1$-$C_6$ alkyl substituted with at least one amino or at least one ($C_1$-$C_4$) alkylamino.

For example, $R_1$ represents a $C_1$-$C_6$ alkyl, a $C_1$-$C_6$ alkyl substituted with at least one hydroxyl, a $C_1$-$C_6$ alkyl substituted with at least one amino or at least one (di)($C_1$-$C_4$) alkylamino, a $C_1$-$C_6$ alkyl substituted with at least one nitrogenous heterocycle chosen from imidazolyl, pyrrolidinyl and piperidyl.

According to at least one embodiment of the disclosure, $R_1$ and $R_6$ together, with the nitrogen to which they are attached, form a heterocycle, wherein the heterocycle can be chosen from imidazoles, piperazines, pyrrolidines and diazepans, which is optionally substituted.

When $R_2$, $R_3$, $R_4$ and $R_5$ represent a substituted alkyl, this alkyl may be substituted for example with a group chosen from OH, $OR_9$, $NH_2$, $NHR_{10}$, $NR_{11}R_{12}$ and $SR_9$ in which $R_9$, $R_{10}$, $R_{11}$ and $R_{12}$, which may be identical or different, are as defined previously.

Examples that may be mentioned include methyl, ethyl, hydroxyethyl, aminoethyl, propyl and butyl.

According to at least one variant, $R_2$, $R_3$, $R_4$ and $R_5$ independently represent a hydrogen atom or a $C_1$-$C_4$ alkyl such as methyl, ethyl, propyl, isopropyl, butyl or tert-butyl, or $R_4$ and $R_5$ together form a 5- to 8-membered heterocycle. According to at least one embodiment, $R_4$ and $R_5$ together form a saturated or unsaturated, 5- to 8-membered and for example 5- to 6-membered ring, such as a cyclopentane or cyclohexane, which is optionally substituted.

According to at least one embodiment, $R_2$, $R_3$, $R_4$ and $R_5$ independently represent a hydrogen atom or a $C_1$-$C_4$ alkyl such as methyl, ethyl, propyl, isopropyl, butyl or tert-butyl.

According to one embodiment, U represents CR or N, and R represents a hydrogen atom, a $C_1$-$C_4$ alkyl, a $C_1$-$C_4$ alkoxy optionally substituted with at least one hydroxyl, or a (di)($C_1$-$C_4$)alkylamino in which the alkyl is optionally substituted with at least one hydroxyl.

For example, U represents CR or N, and R represents a hydrogen atom, a methyl, a methoxy, a 2-hydroxymethoxy, a methylamino, a dimethylamino or hydroxyethylamino or a dihydroxyethylamino or methyl(hydroxyethyl)amino.

For further example, U represents CR or N, and R represents a hydrogen atom, a methyl radical or a 2-hydroxyethoxy.

According to at least one embodiment of the disclosure, X represents a hydroxyl; the group $NR'_1R''_1$, wherein $R'_1$ and $R''_1$ are chosen independently from a hydrogen atom; and a $C_1$-$C_6$ alkyl optionally substituted with at least one hydroxyl. For example, X represents a hydroxyl; a group $NR'_1R''_1$, wherein $R'_1$ and $R''_1$ are independently chosen from a hydrogen atom; a methyl; and a 2-hydroxyethyl.

According to another embodiment, when $R'_1$ and $R''_1$, together with the nitrogen atom, to which they are attached, form a heterocycle, this heterocycle cab be chosen from pyrrolidine, piperidine, homopiperidine, piperazine, homopiperazine and morpholine, which is optionally substituted with at least one radical chosen from a halogen atom, amino, (di)($C_1$-$C_4$)alkylamino, hydroxyl, carboxyl, (di)alkylcarboxamido, ($C_1$-$C_2$)alkoxy and $C_1$-$C_4$ alkyl, optionally substituted with at least one radical chosen from hydroxyl, amino, (di)alkylamino, alkoxy, carboxyl and sulfonyl. For example, this heterocycle can be chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)-aminopyrrolidine, piperidine, 2,6-dimethylpiperidine, 2-carboxypiperidine, 2-carboxamido-piperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methyl-homopiperazine, N-(2-hydroxyethyl)homopiperazine and morpholine.

For further example, this heterocycle can be chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, 4-hydroxypiperidine, homopiperidine, homopiperazine, N-methylhomopiperazine, N-(2-hydroxyethyl)homopiperazine and morpholine.

In accordance with at least one embodiment of the disclosure, $R_1$ and $R''_1$ form, together with the nitrogen atom to which they are attached, a 5-membered ring such as pyrrolidine, 3-hydroxypyrrolidine, 3-aminopyrrolidine or 3-dimethylaminopyrrolidine.

According to at least one embodiment of the disclosure, V represents:

an oxygen atom;

a group $NR'_1$ in which $R'_1$ represents a hydrogen atom or a $C_1$-$C_6$ alkyl optionally substituted with at least one hydroxyl.

For example, V represents an oxygen atom or an NH group.

According to another embodiment of the disclosure, X and U, or, respectively, V and U, form a 6-membered ring such as morpholine, optionally substituted with at least one $C_1$-$C_4$alkyl group, which are for example, unsubstituted.

According to another embodiment of the disclosure, Y, which may be identical or different, represent a hydroxyl; a $C_1$-$C_4$ alkyl; a halogen atom; an oxygen atom substituted with a $C_1$-$C_4$ alkyl which may be substituted with at least one hydroxyl; or group $NR'_2R'_3$;

R'$_2$ and R'$_3$, which may be identical or different, may be chosen from a hydrogen atom; a C$_1$-C$_4$ alkylcarbonyl; an aminocarbonyl; a C$_1$-C$_6$ alkyl optionally substituted with at least one hydroxyl;

R'$_2$ and R'$_3$ may form, together with the nitrogen atom to which they are attached, a saturated 5- to 7-membered heterocycle.

In at least one embodiment of the disclosure, the heterocycle can be chosen from pyrrolidine, piperidine, homopiperidine, piperazine, homopiperazine and morpholine, wherein the ring is optionally substituted with at least one radical chosen from a halogen, amino, (di)(C$_1$-C$_4$)alkylamino, hydroxyl, carboxyl, (di)alkylcarboxamido, (C$_1$-C$_2$) alkoxy and C$_1$-C$_4$ alkyl, optionally substituted with at least one radical chosen from hydroxyl, amino, (di)alkylamino, alkoxy, carboxyl and sulfonyl.

Two radicals Y borne by two adjacent carbon atoms may form, together with the carbon atoms to which they are attached, a saturated or unsaturated, aromatic or non-aromatic 5- or 6-membered cyclic or heterocyclic group.

For example, Y, which may be identical or different, represent a hydroxyl; a methyl; a chlorine atom; a 2-hydroxyethoxy; an amino; or a (2-hydroxyethyl)amino.

The term "acid-addition salts" means the salts of physiologically acceptable organic or mineral acids and the compounds of formula (I) and/or (II).

The leuco form compounds of formula (I), and dyes of azomethine type comprising a pyrazolopyridine unit of formula (II), may be optionally salified with strong mineral acids, for instance HCl, HBr, HI, H$_2$SO$_4$, H$_3$PO$_4$, or organic acids, for instance acetic acid, lactic acid, tartaric acid, citric acid or succinic acid, benzenesulfonic acid, para-toluenesulfonic acid, formic acid or methanesulfonic acid.

In the context of the disclosure, the term "derivative of formula (I) and/or (II)" means any mesomeric form, salt or isomer.

They may also be in the form of solvates, for example a hydrate or a solvate of a linear or branched alcohol such as ethanol or isopropanol.

The present disclosure makes it possible, for example, rapidly to obtain chromatic colorations that can be resistant to the various attacking factors to which the hair may be subjected, and especially to shampoos and light, these colorations can be removed and then reformed just as quickly.

The leuco form compounds of formula (I) are colorless or weakly colored, and the corresponding azomethine comprising a pyrazolopyridine unit of formula (II) colored and coloring species. It is possible to modify the structure of the compounds of formula (I) to obtain the compounds of formula (II) by adding an oxidizing agent, and, conversely, it is possible to modify the structure of the compounds of formula (II) to obtain the compounds of formula (I) by adding a reducing agent. This structure modification may be facilitated by modifying the pH and/or the temperature. Formation of the compounds of formula (I) can thus be promoted by acidic pH and/or reducing the temperature, and formation of the compounds of formula (II) can be promoted by basic pH and/or raising the temperature. Such behavior makes it possible for example to readily modify the coloration of keratin fibers.

As examples of the dyes of azomethine type comprising a pyrazolopyridine unit of formula (II), mention may be made of the compounds presented below:

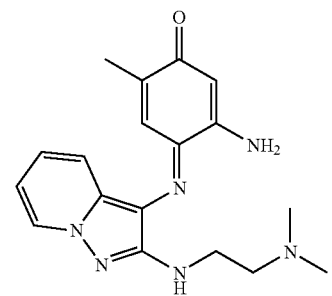

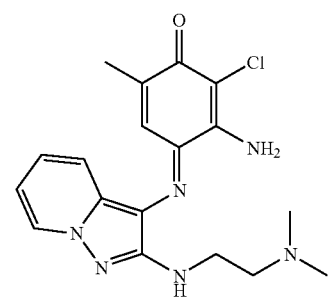

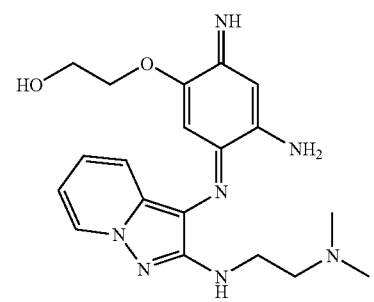

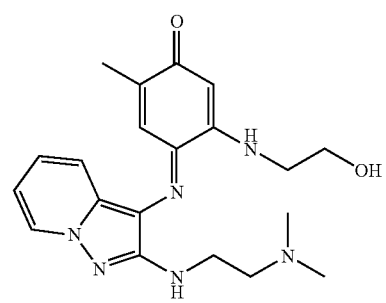

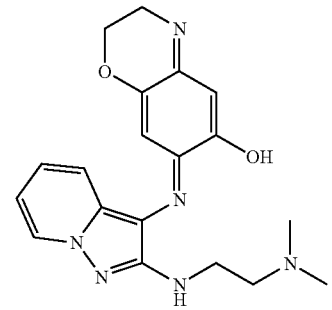

-continued
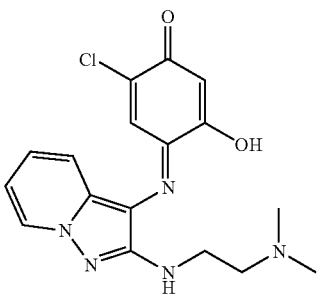
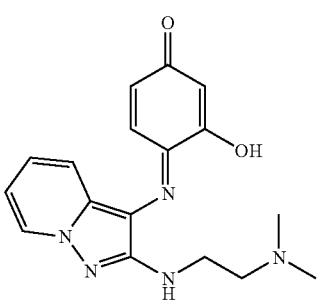
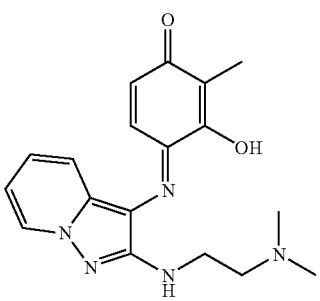
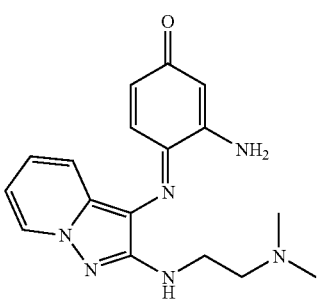
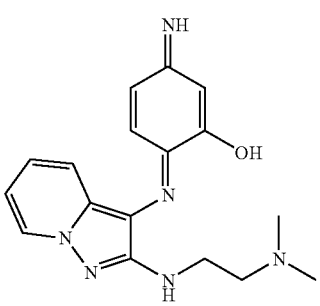
-continued
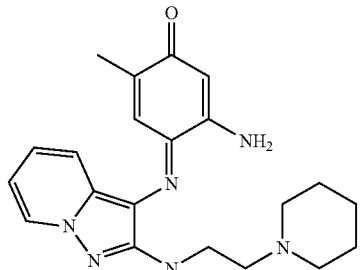
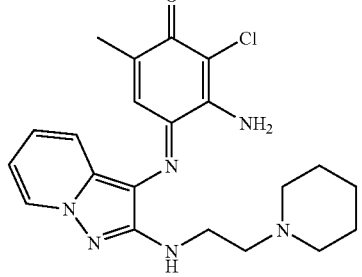
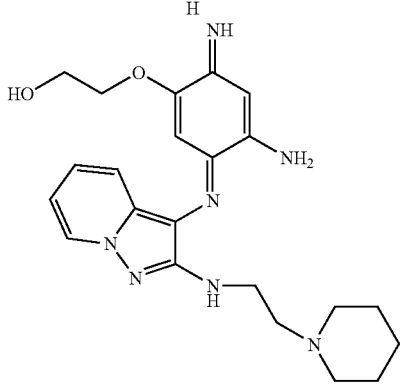
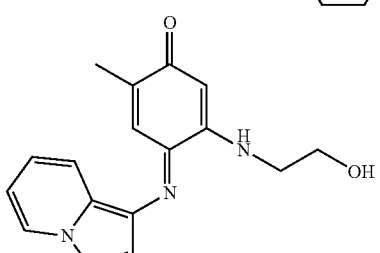
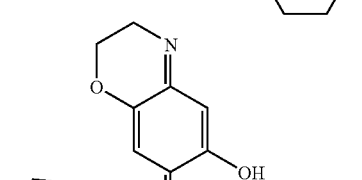
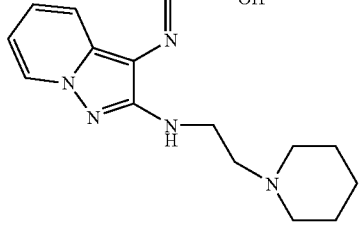

-continued
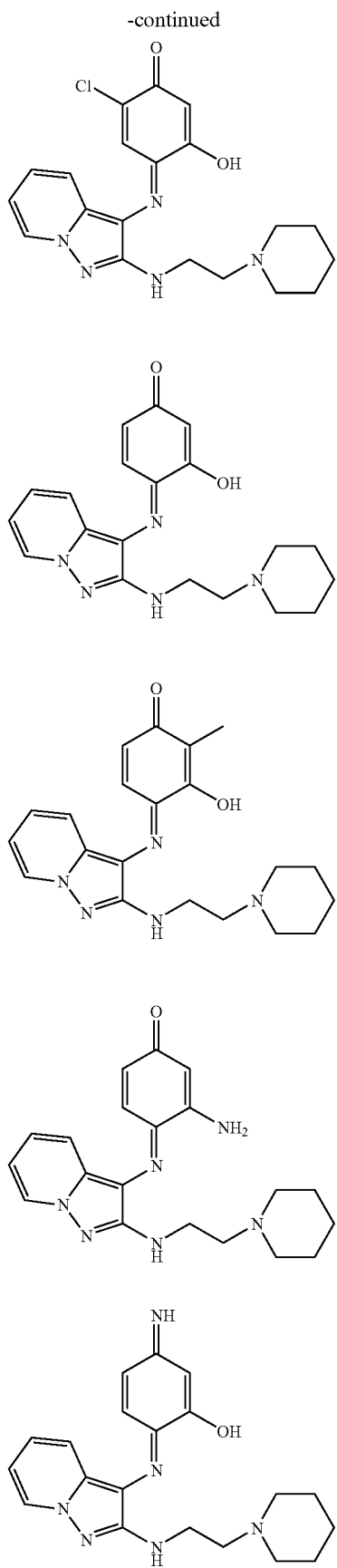
-continued
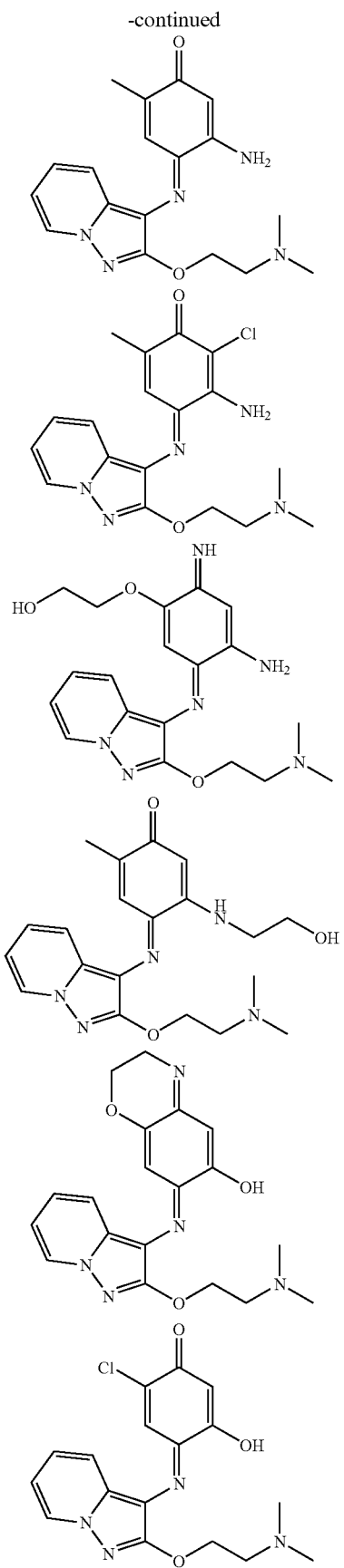

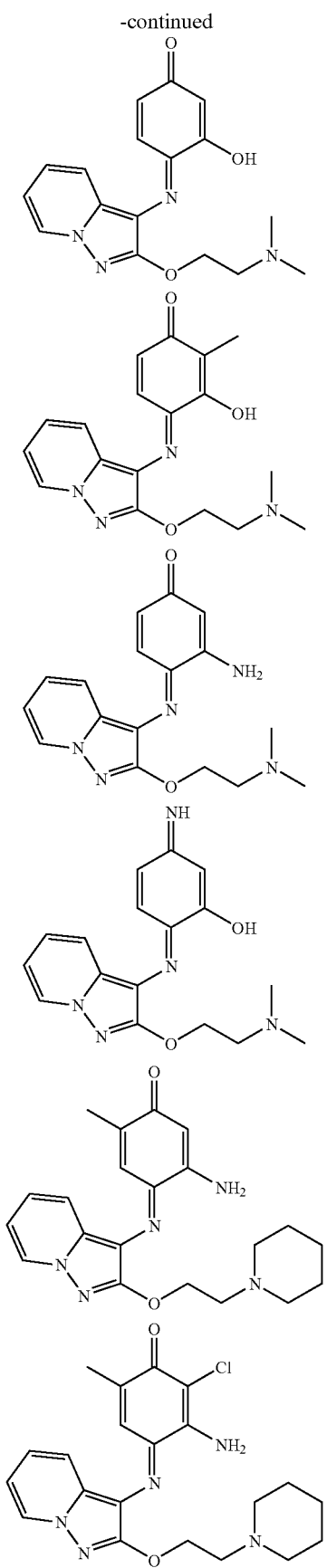
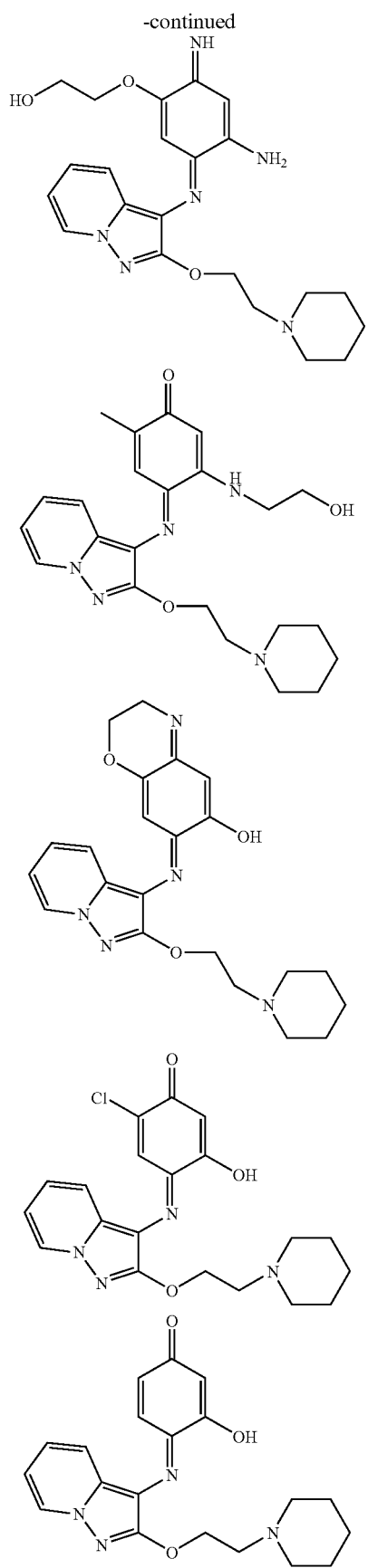

-continued
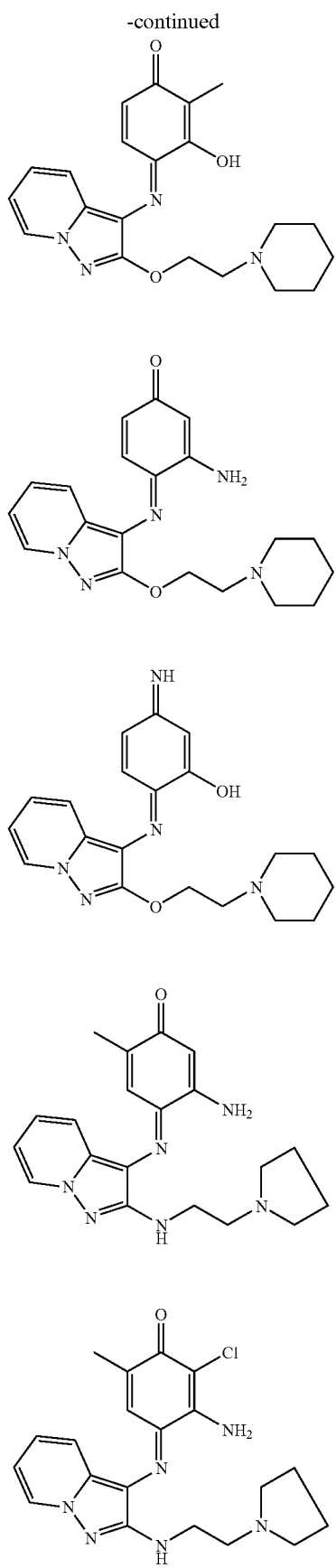
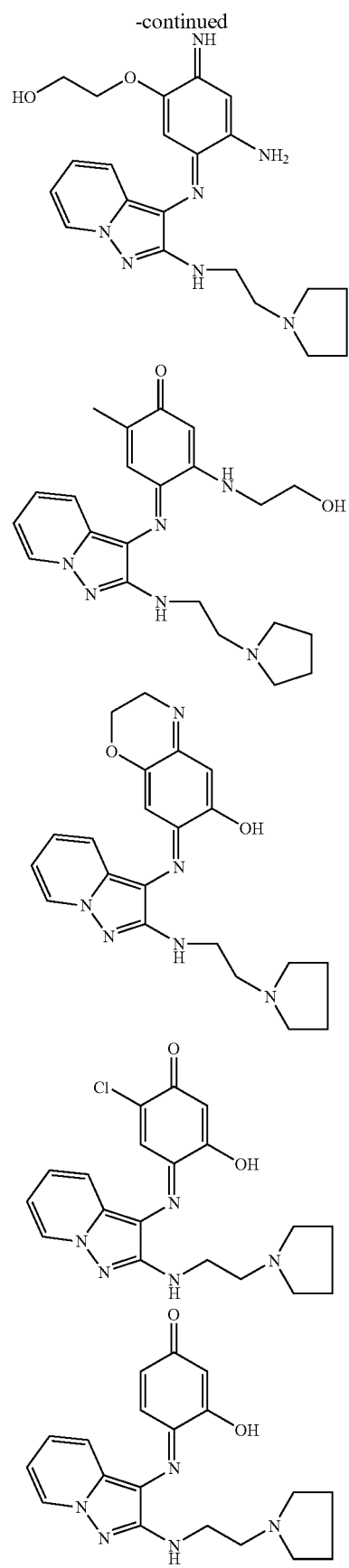

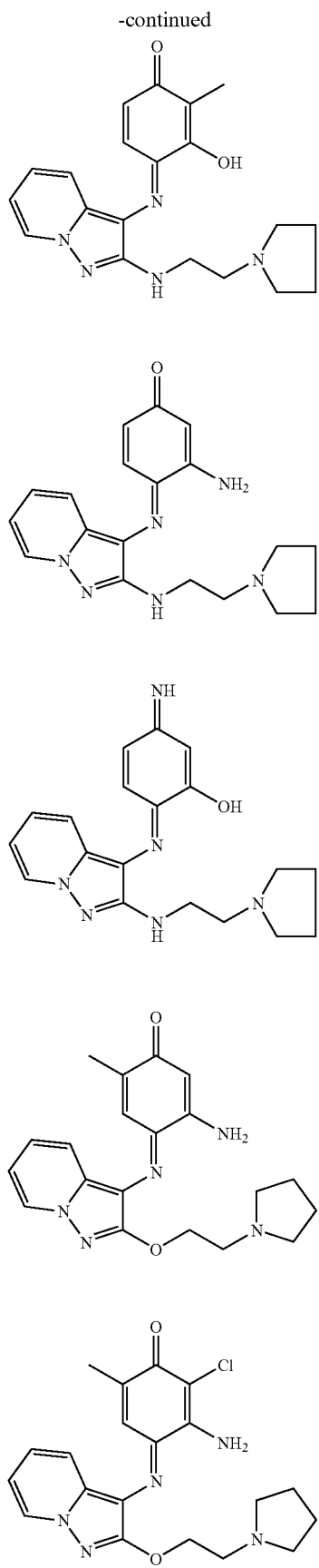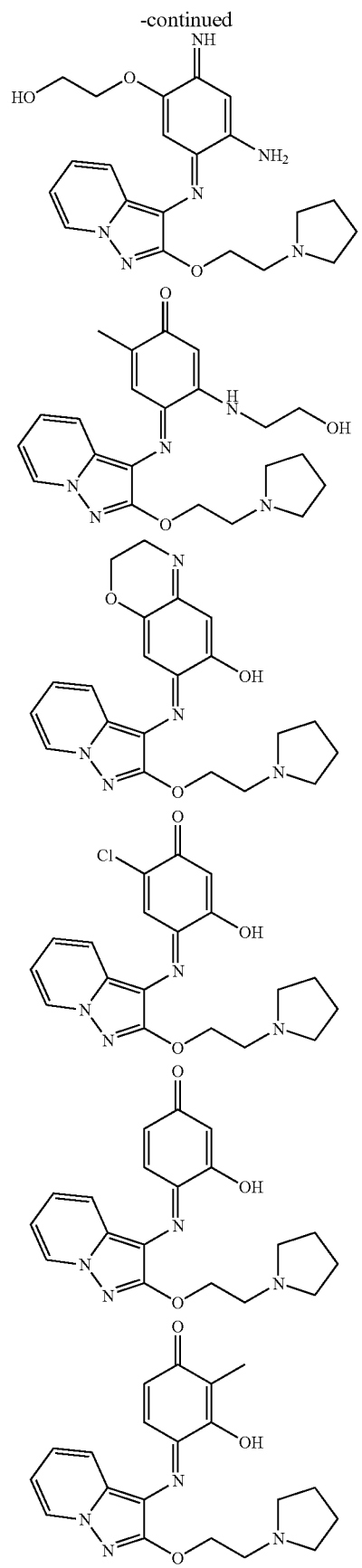

-continued
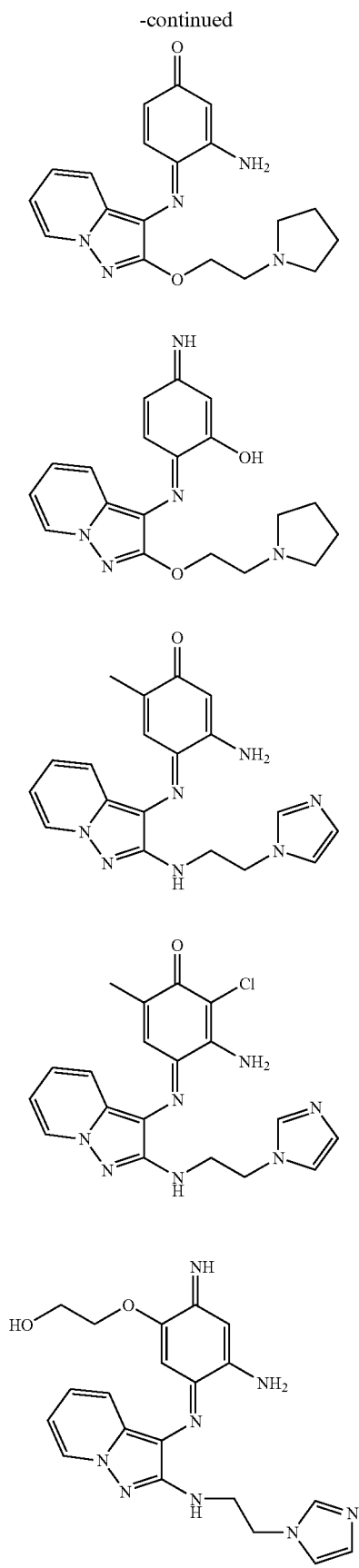
-continued
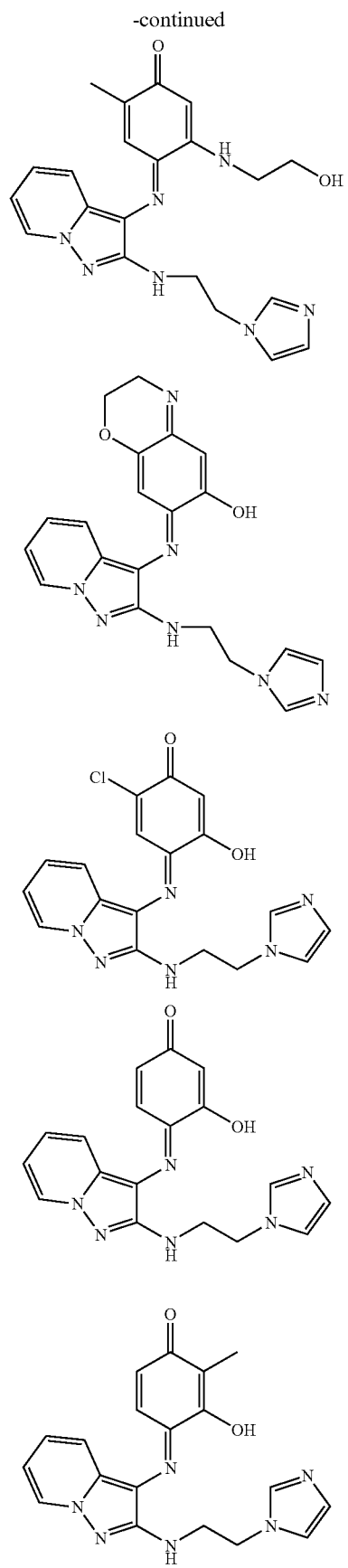

-continued
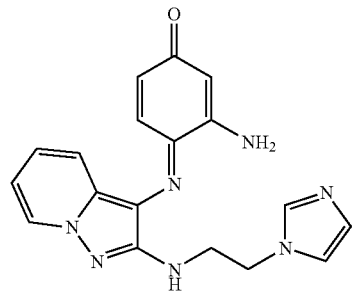
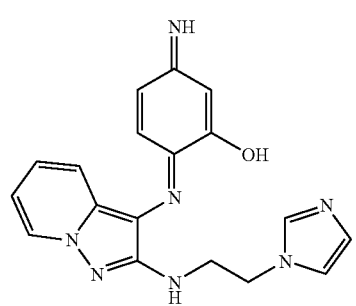
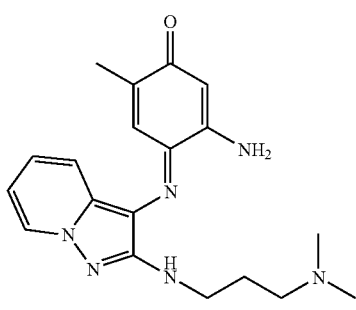
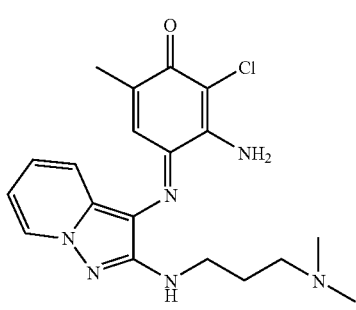
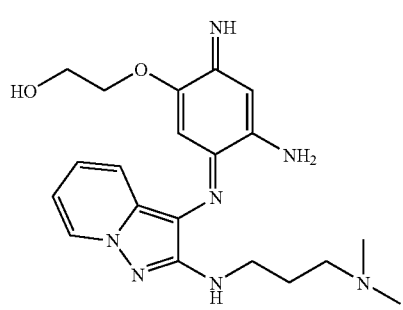
-continued
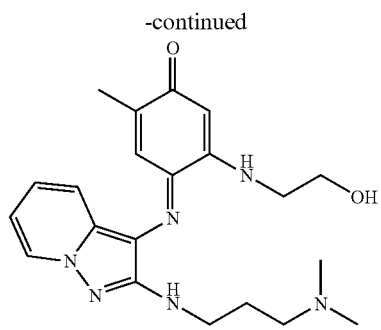
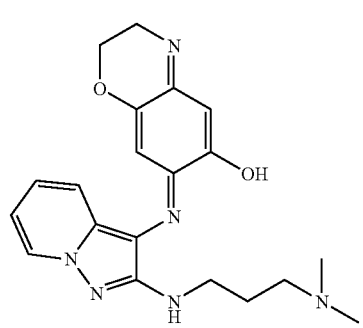
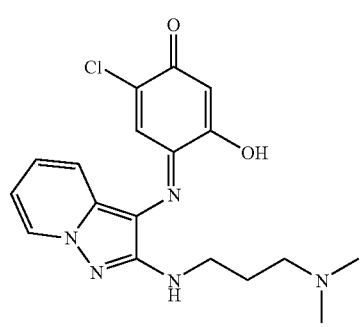
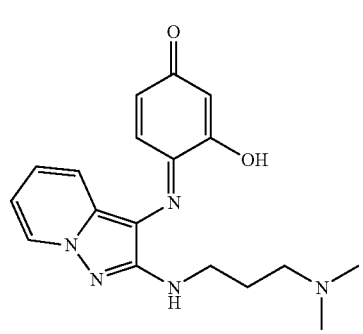

-continued
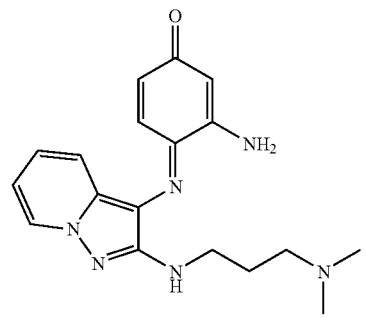
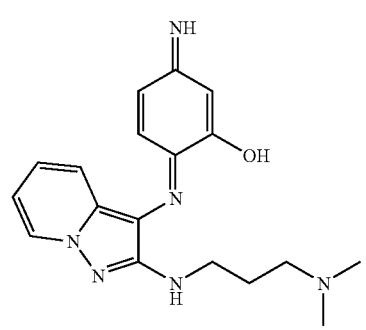
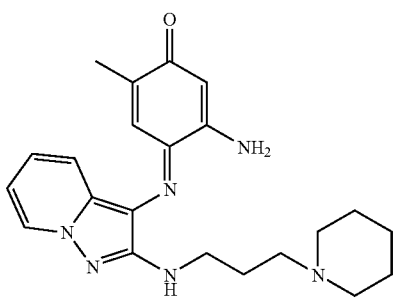
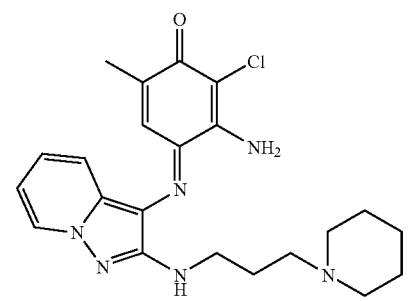
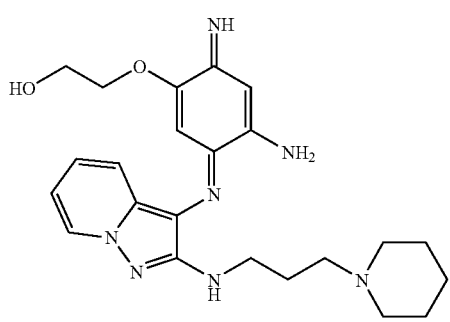
-continued
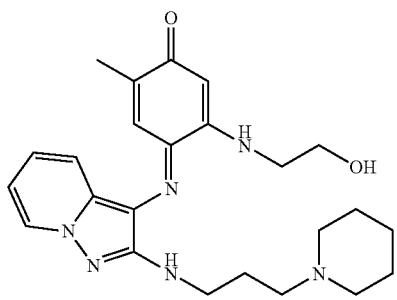
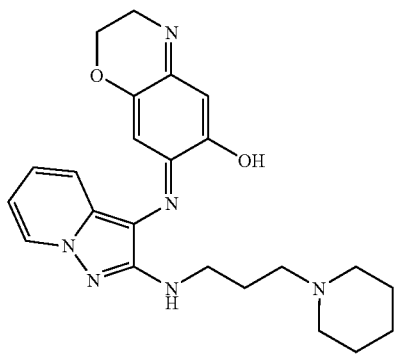
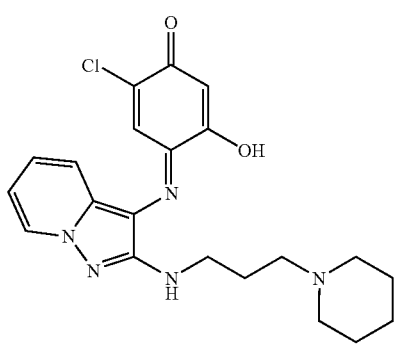
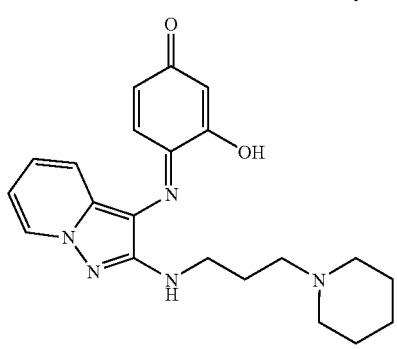
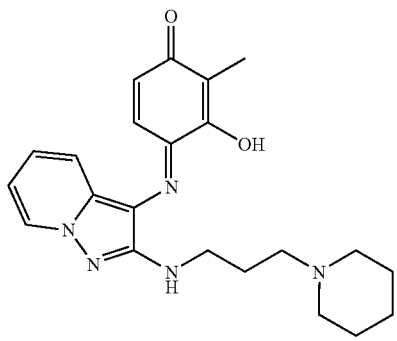

-continued
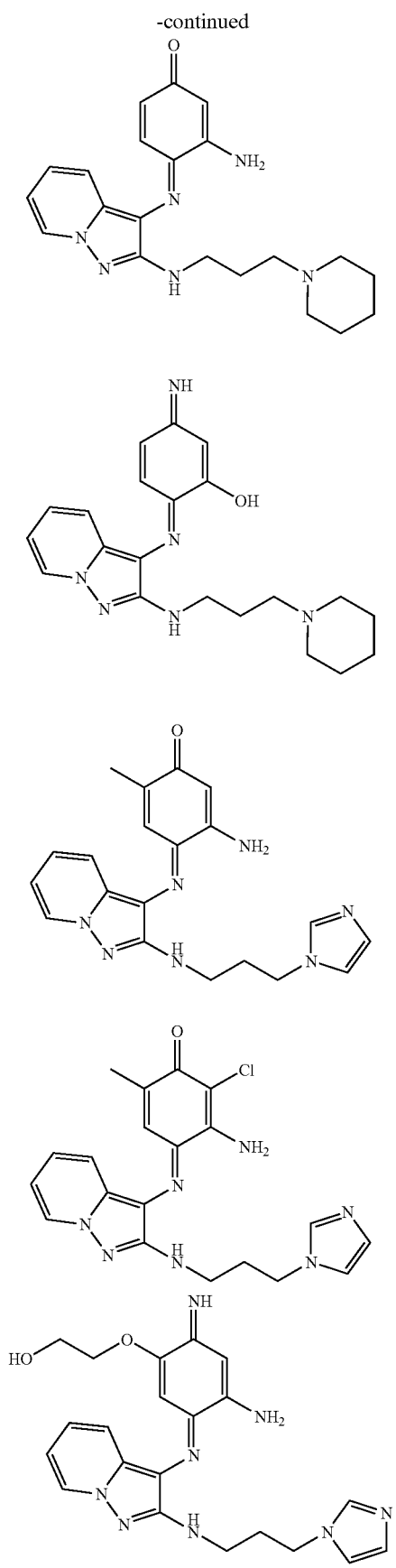
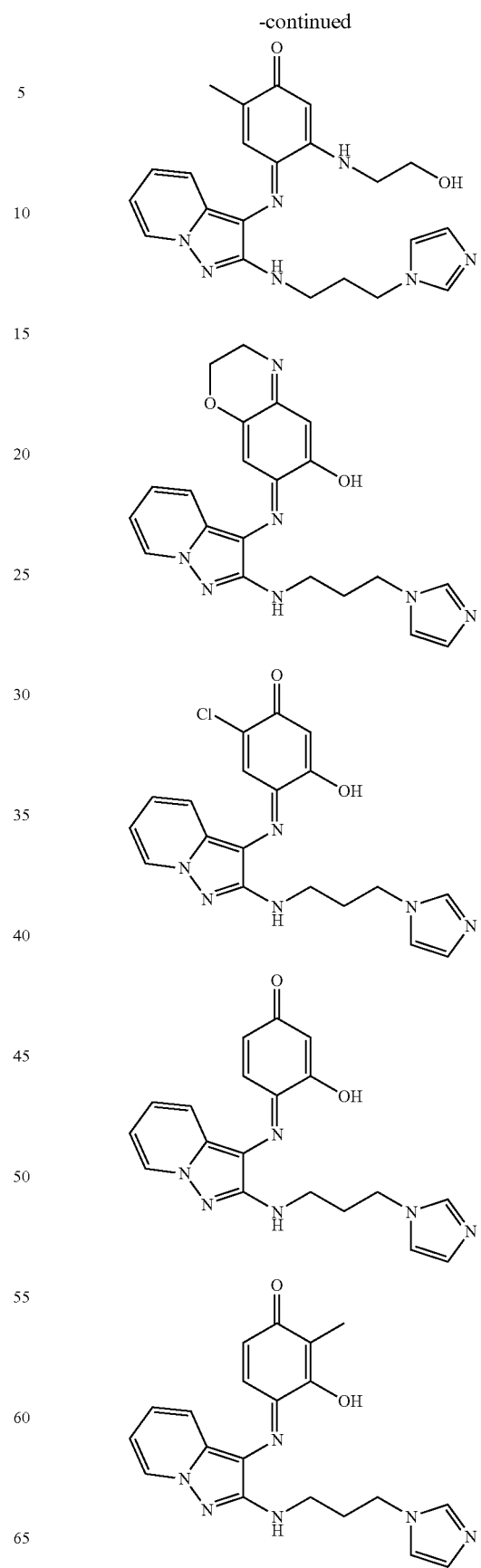

-continued
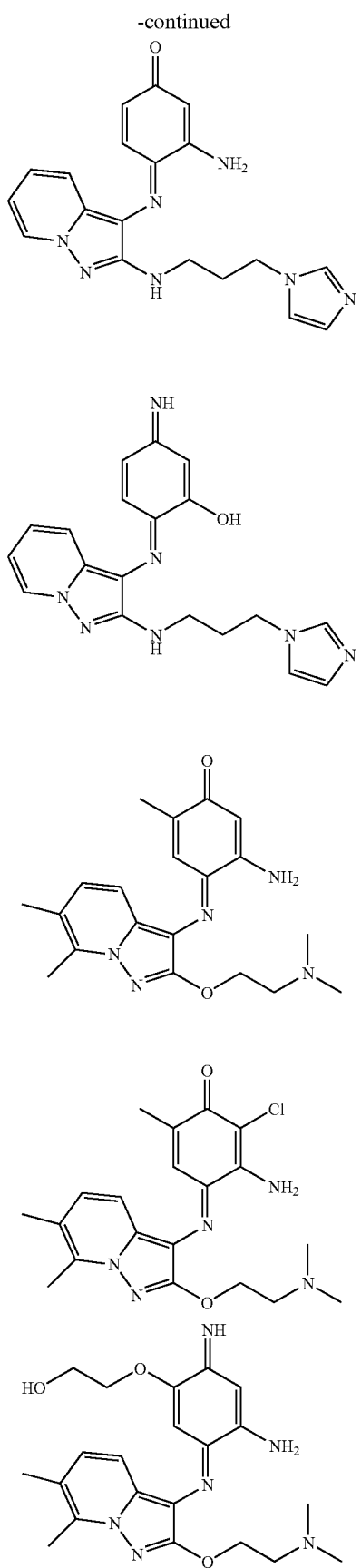
-continued
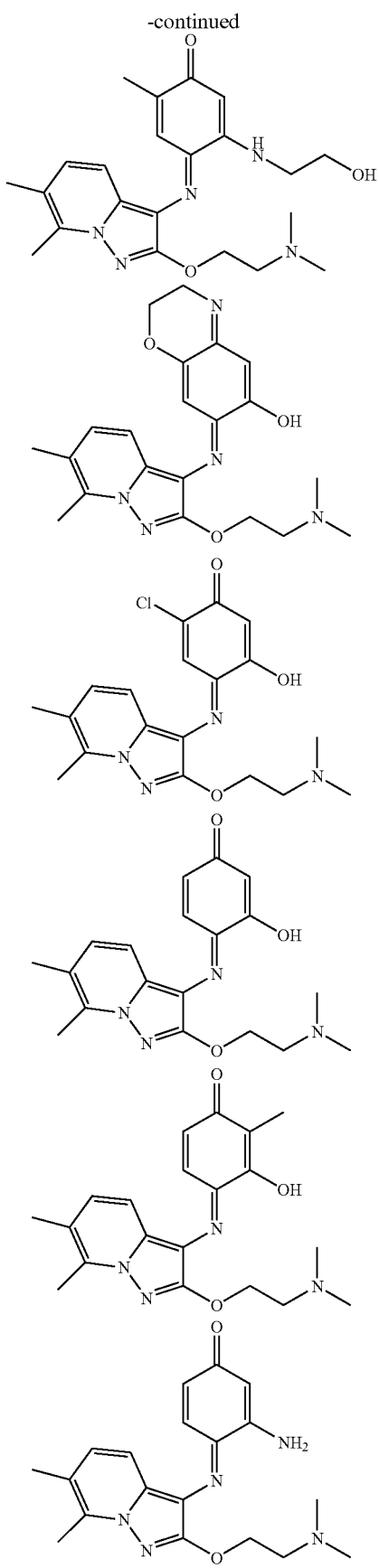

-continued
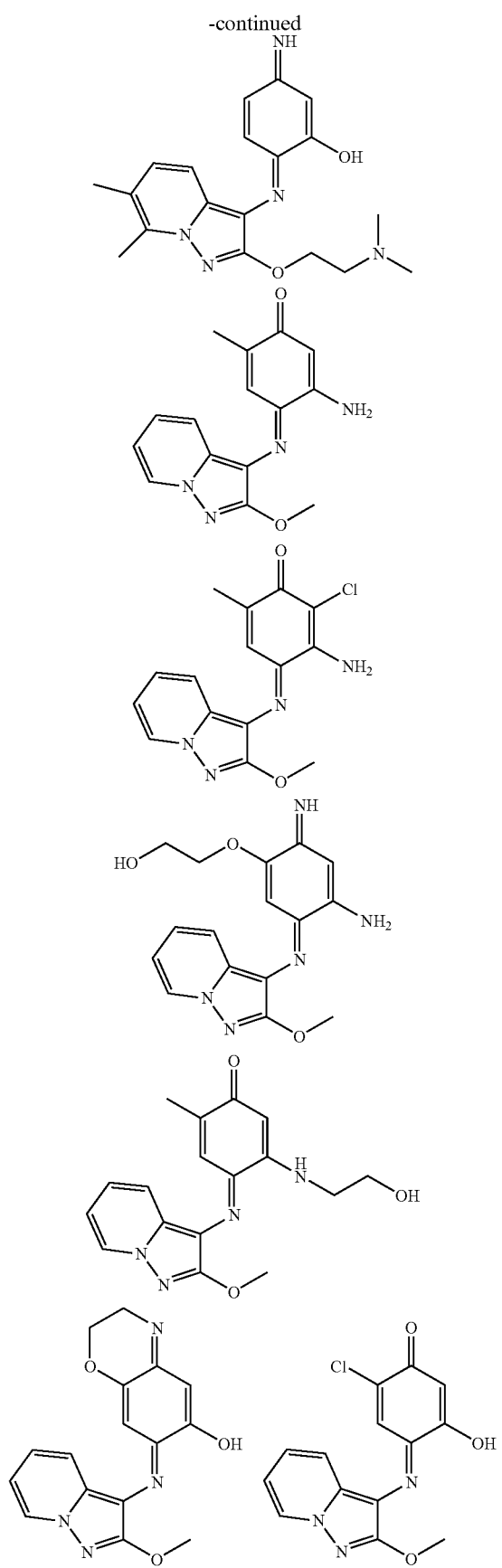
-continued
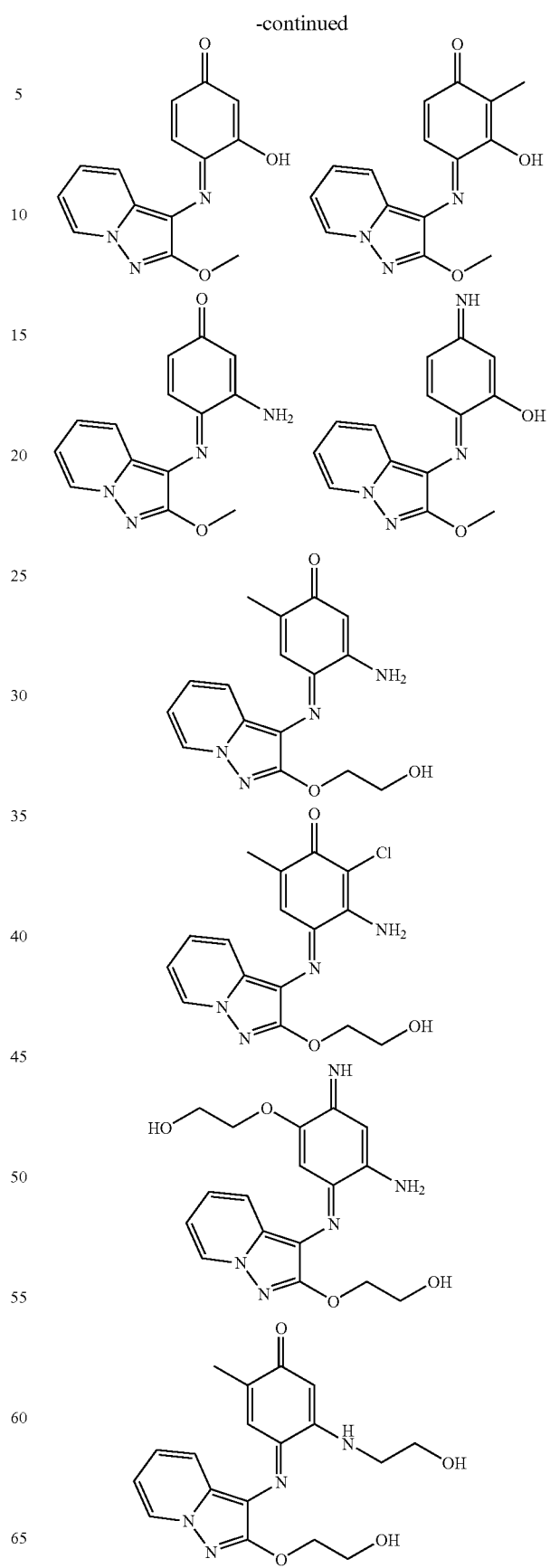

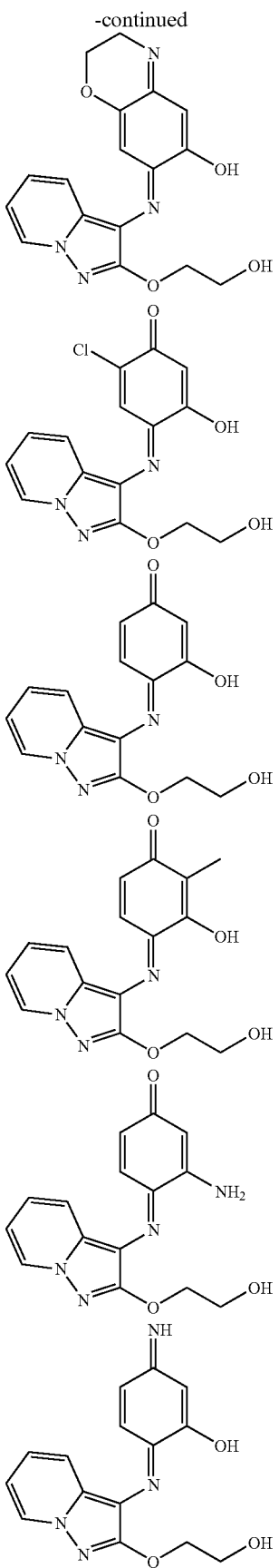
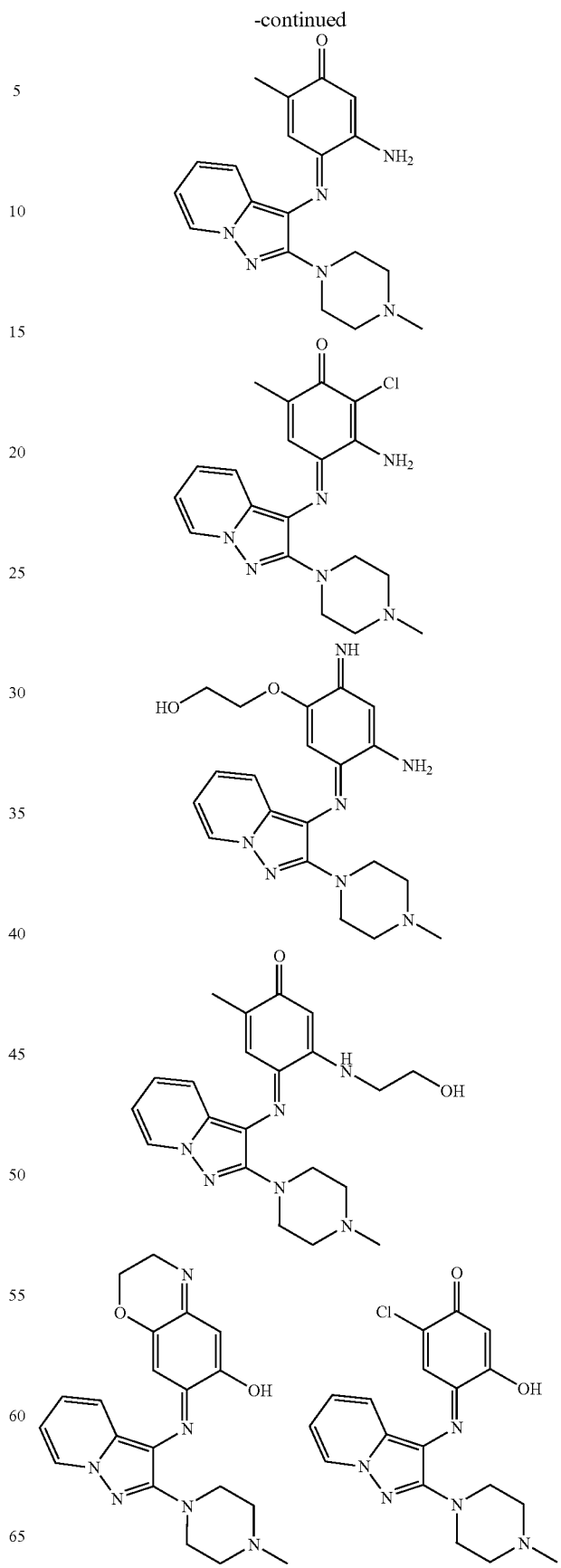

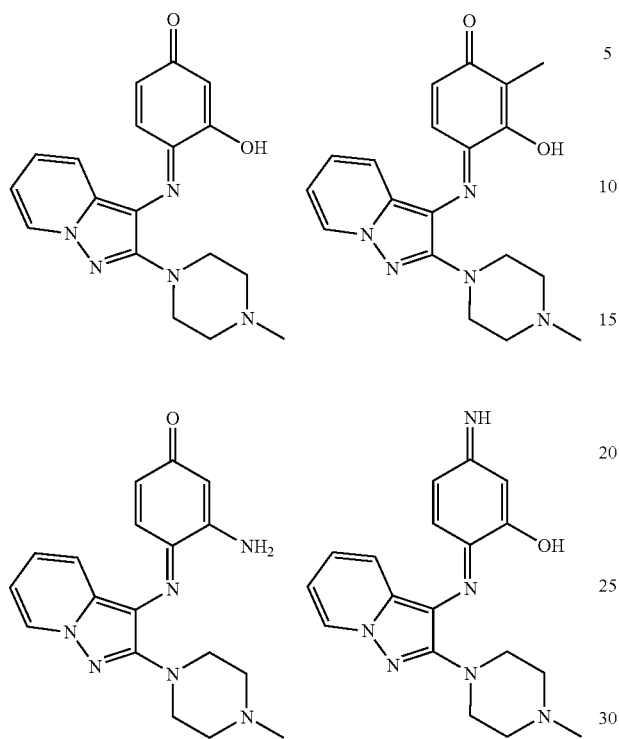
and also the isomers, tautomers, mesomers, solvates and addition salts thereof, and the corresponding leuco form compounds of formula (I).
For example, the dyes of azomethine type comprising a pyrazolopyridine unit of formula (II) are chosen from the following compounds:
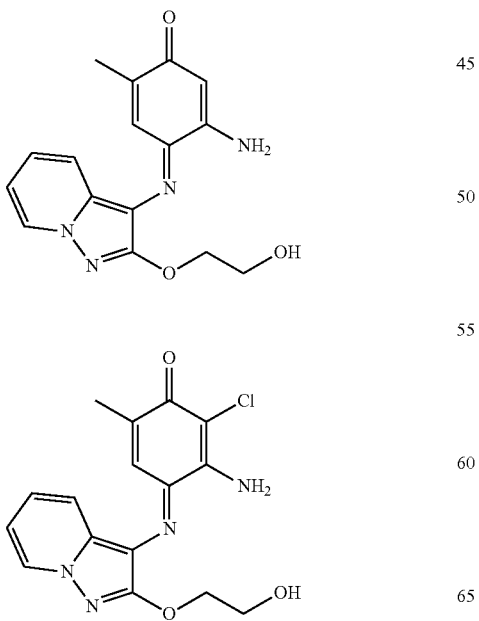
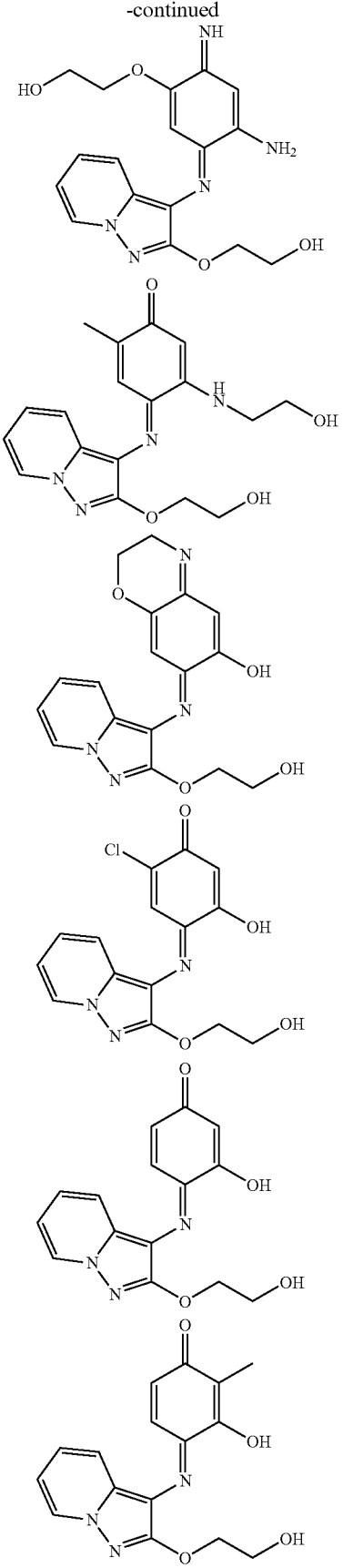

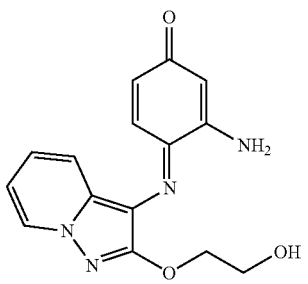
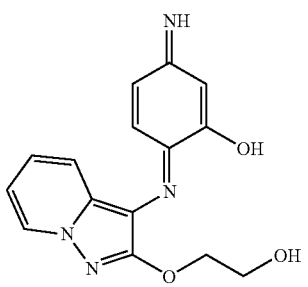
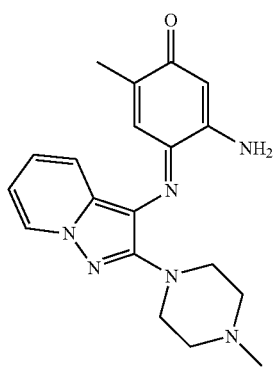
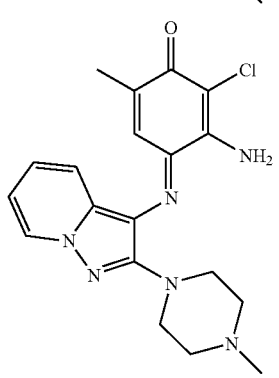
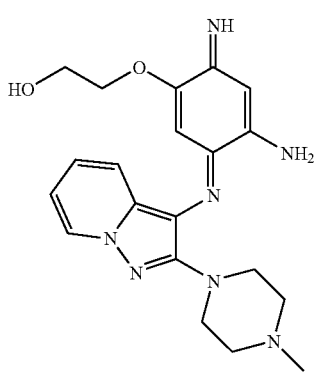
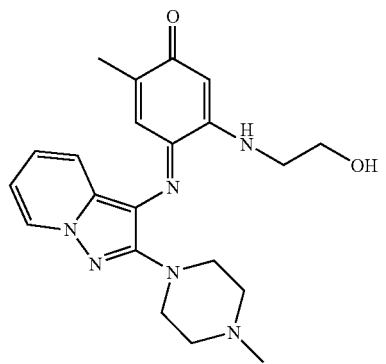
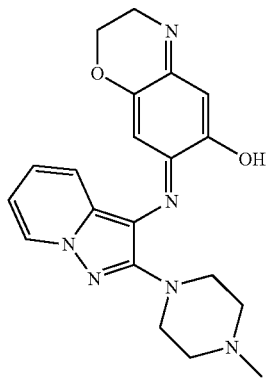
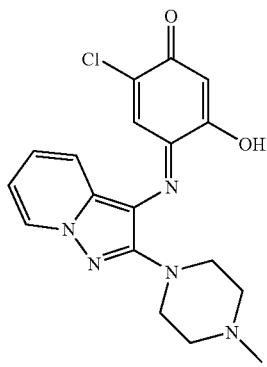
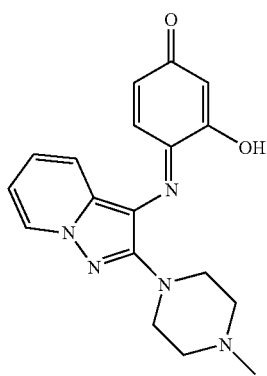

-continued
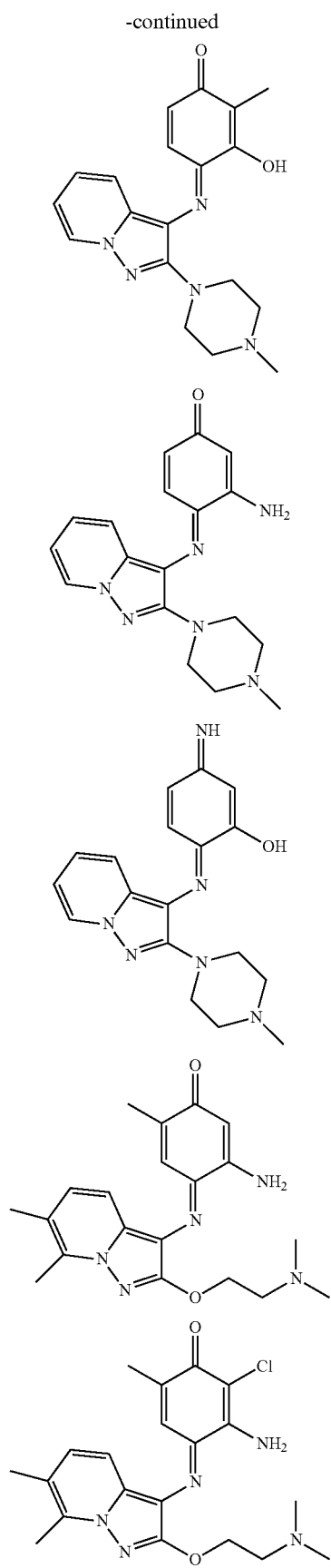
-continued
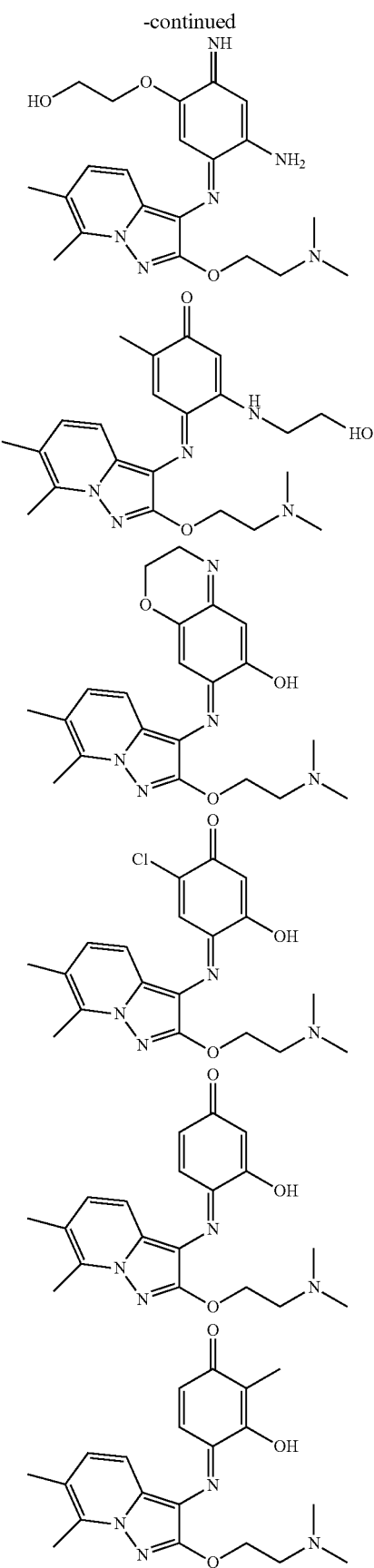

-continued
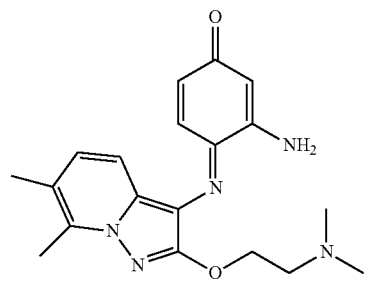
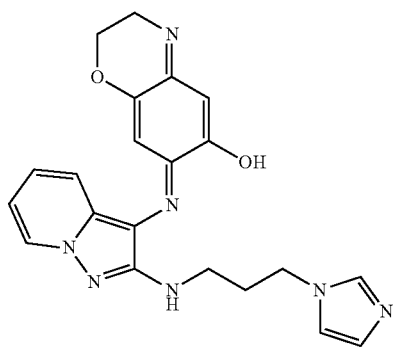
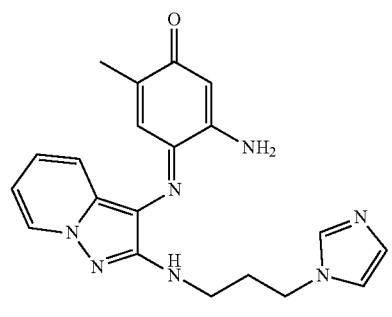
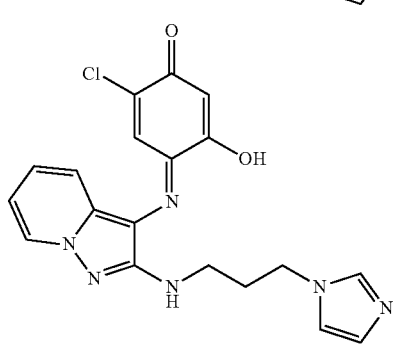
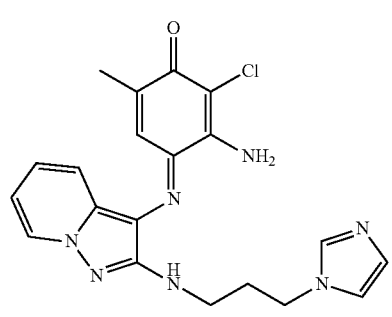
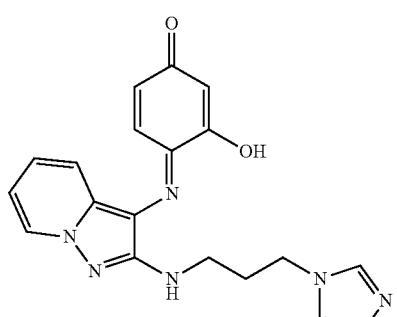
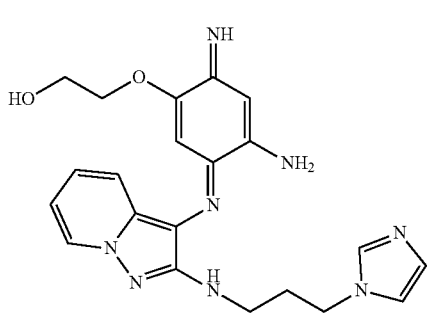
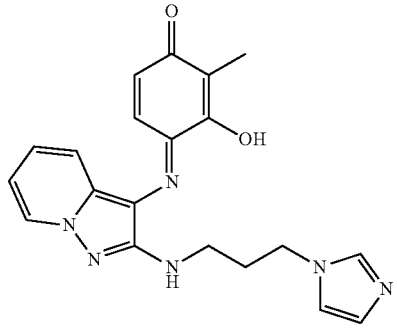
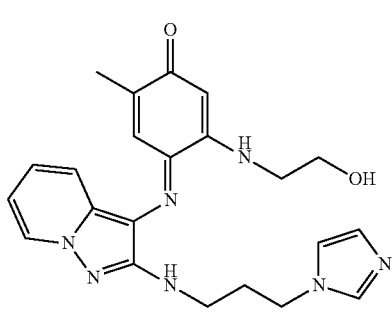
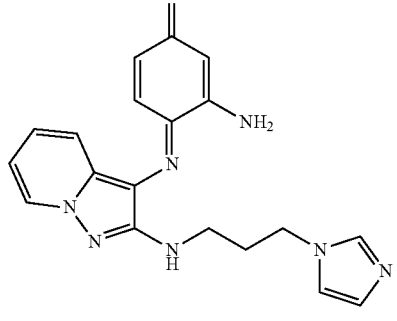

-continued
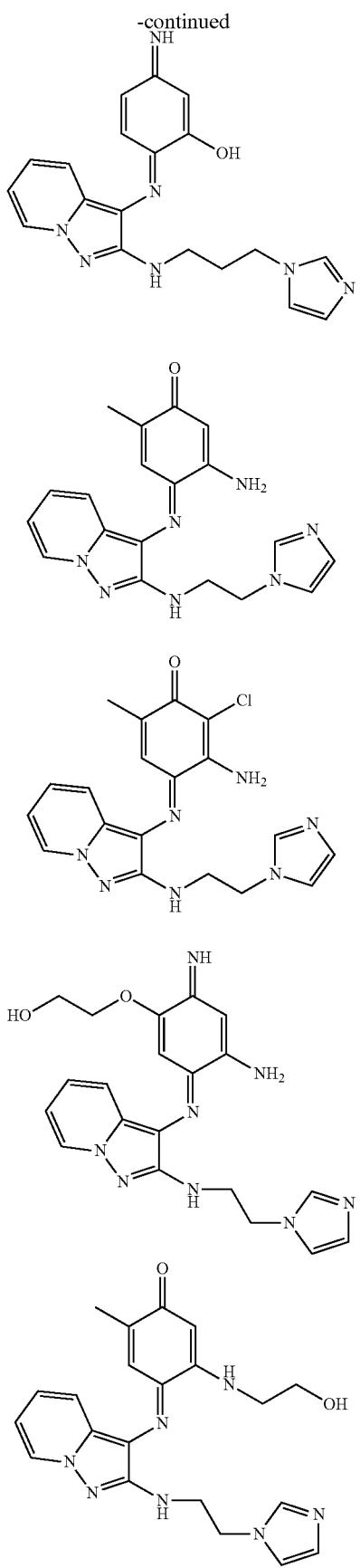
-continued
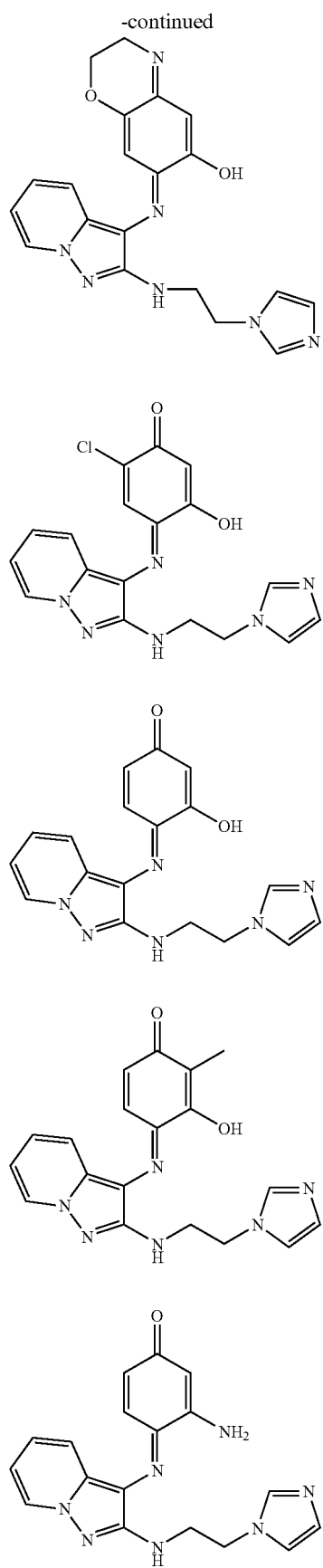

-continued
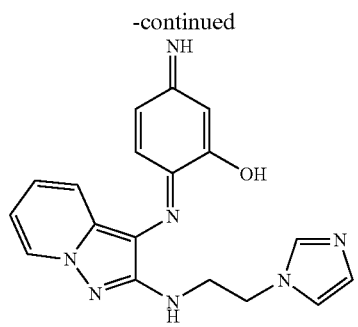
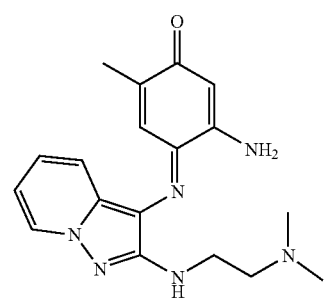
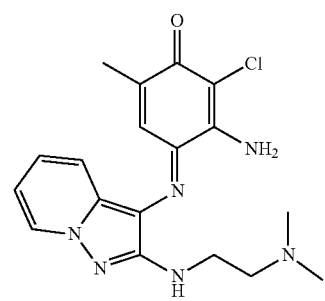
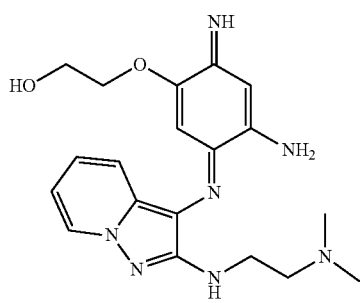
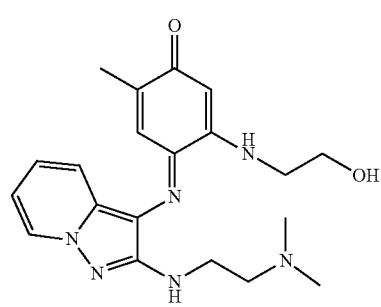
-continued
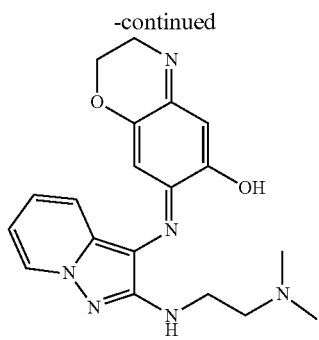
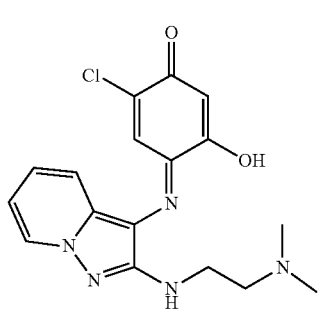
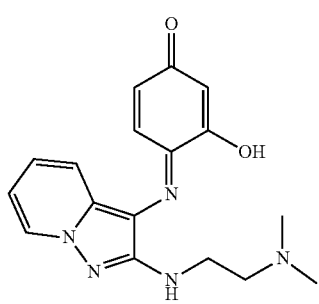
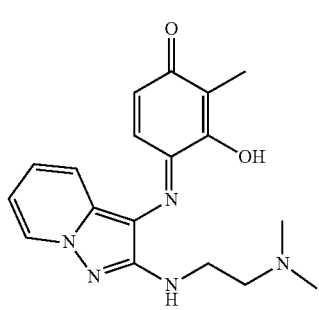
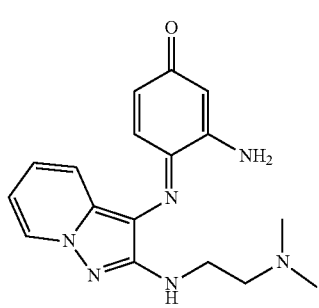

-continued
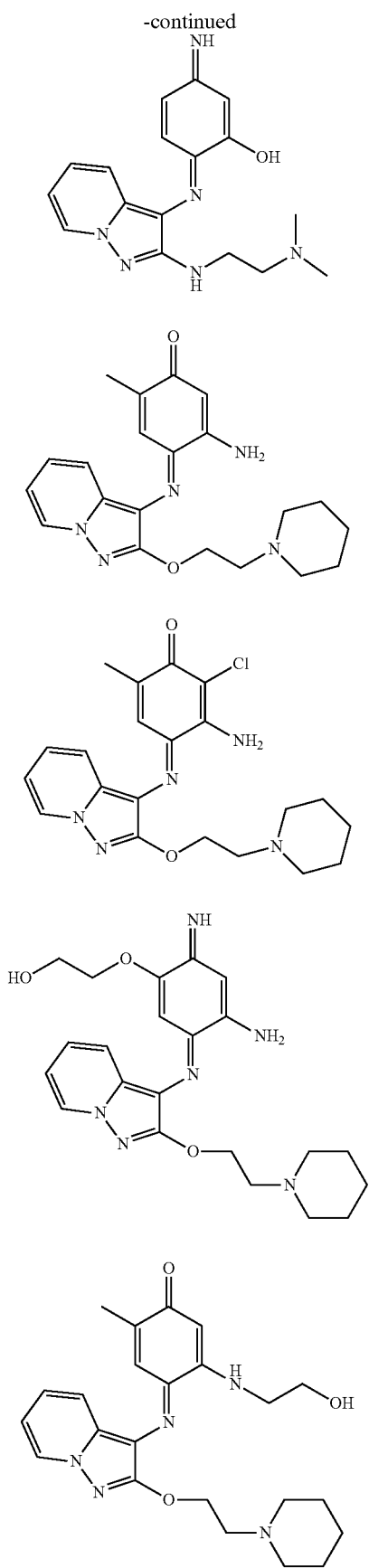
-continued
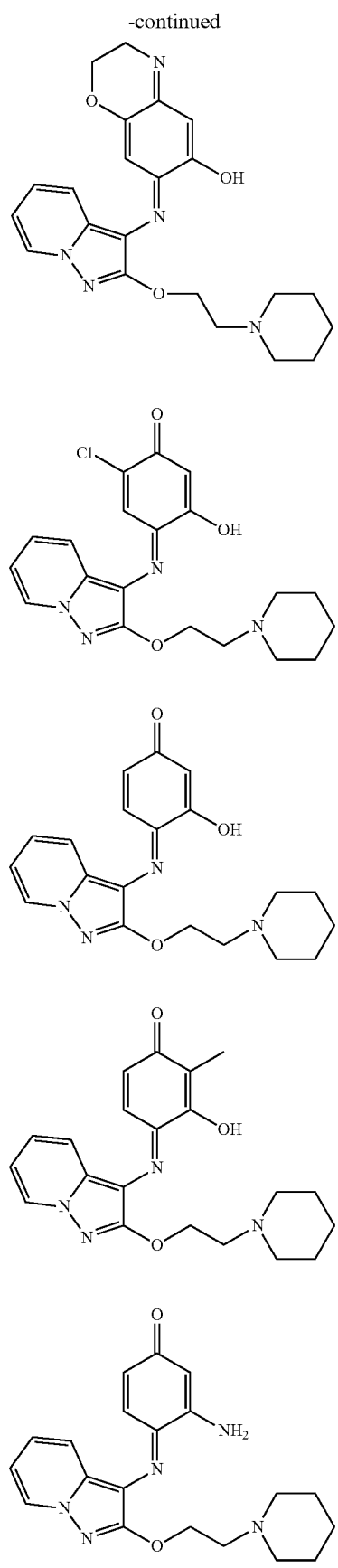

-continued
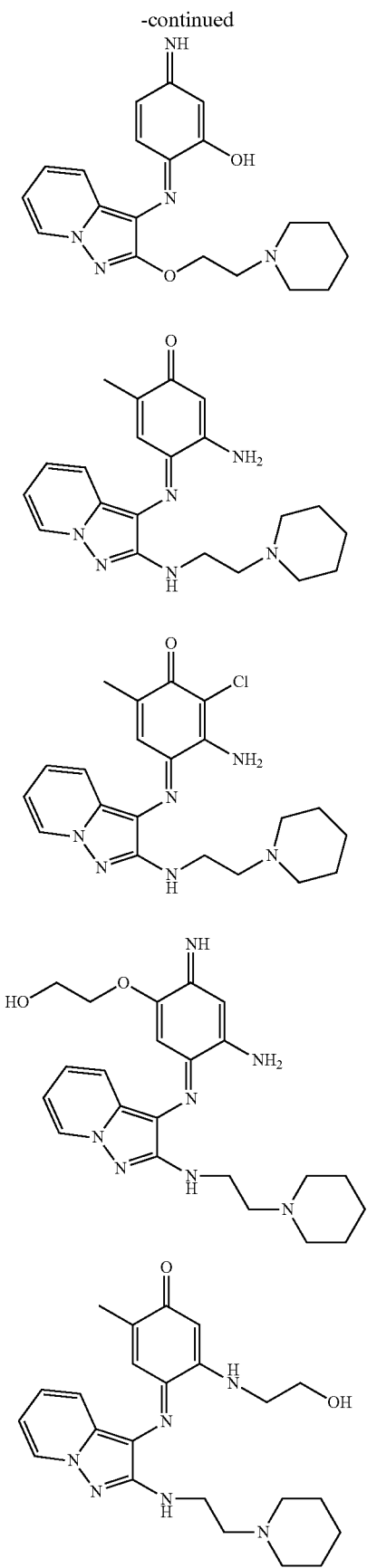
-continued
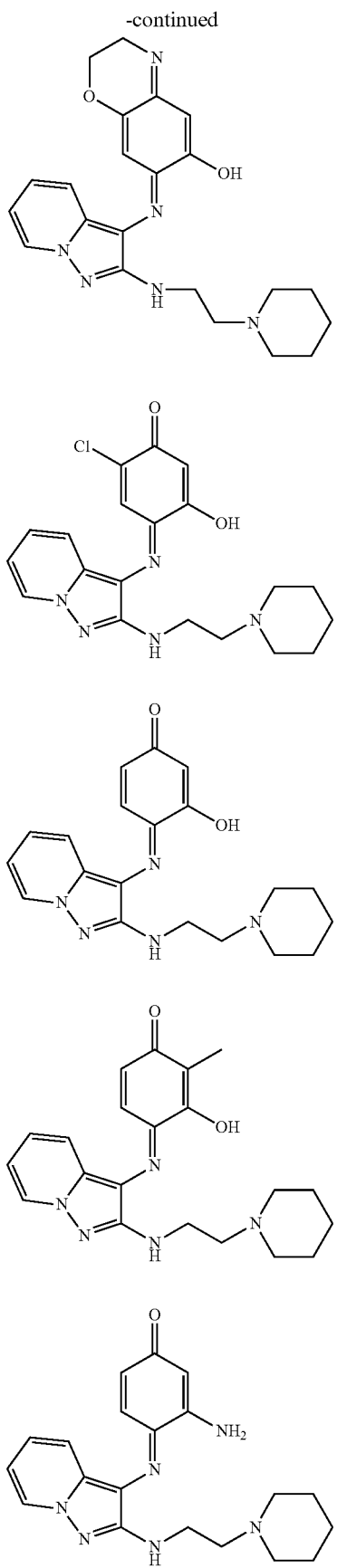

-continued

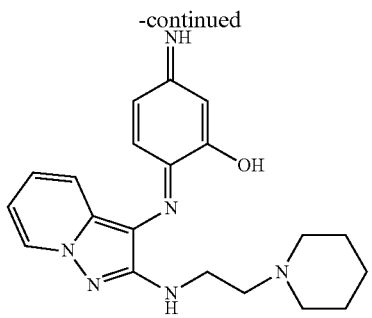

and also the isomers, mesomers, tautomers, solvates and addition salts thereof, and the corresponding leuco form compounds of formula (I).

According to at least one embodiment, the azomethine dyes are chosen from the compounds of formula (IIa) and (IIb):

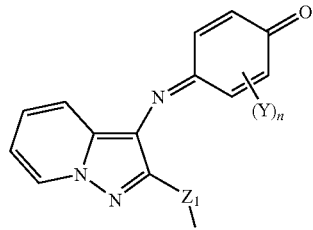
(IIa)

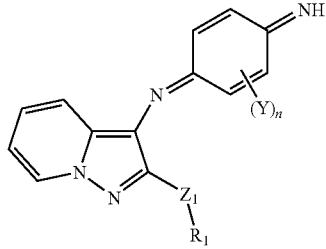
(IIb)

in which $R_1$ and $Z_1$, Y and n are as defined previously. According to at least one embodiment, $Z_1$ is chosen from an oxygen atom and a group $NR_6$. When $Z_1$ represents an oxygen atom, $R_1$ is for example a hydroxyalkyl or an aminoalkyl optionally substituted with at least one alkyl on the nitrogen atom. When $Z_1$ is $NR_6$, $R_1$ can form with $R_6$ a piperazinyl ring, or $R_6$ is hydrogen and $R_1$ is an alkyl radical substituted with an imidazole radical.

According to another embodiment, n is 0, 1 or 2, and Y is chosen from hydroxyl, alkyl, hydroxyalkoxy, and halogen.

The compounds of formula (I) and/or (II) may be obtained according to the procedure below:

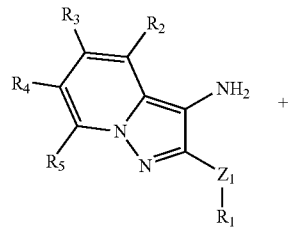

-continued

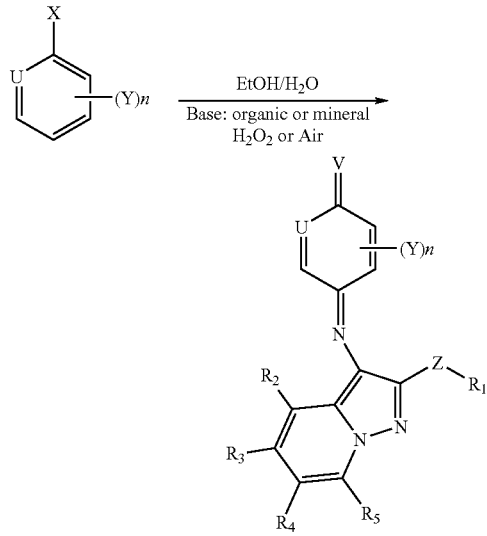

The pyrazolopyridine is weighed out in a beaker and dissolved in water and/or ethanol at room temperature. The coupler is then added, followed by a base such as aqueous ammonia, sodium hydroxide, potassium hydroxide, or a mineral carbonate such as potassium carbonate, or an acetate, in the presence of at least one oxidizing agent. The oxidizing agent(s) may be air, aqueous hydrogen peroxide solution or any other chemical oxidizing agent. The reaction medium becomes colored as soon as the last two reagents are added. The reaction medium thus obtained is stirred for a period of 30 minutes to 24 hours. The product formed is filtered off and then washed with water, and then optionally with isopropyl ether. The compound recovered in powder form is dried at 20° C. under vacuum to constant weight. When there is no precipitation, the compound obtained from this reaction is recovered by evaporating off the solvent and optionally purified on a column of silica. Characterization is performed by NMR spectroscopy and/or mass spectrometry.

Provided herein is also a composition for dyeing keratin fibers, comprising, in a suitable dyeing medium, at least one compound chosen from the leuco form compounds of formula (I), the dyes of azomethine type comprising a pyrazolopyridine unit of formula (II) as described previously, provided that when X is hydroxyl or V is oxygen, at least one Y is hydroxyl or a group $NR'_2R'_3$, the mesomeric forms, isomers and tautomers thereof, and also the acid-addition salts thereof and the solvates thereof, with the exception of the following compound:

and also the mesomeric forms, isomers and tautomers thereof, the acid-addition salts thereof and the solvates thereof.

The at least one compound is chosen from the leuco form compounds of formula (I), the dyes of azomethine type comprising a pyrazolopyridine unit of formula (II), the mesomeric forms, isomers and tautomers thereof, and also the acid-addition salts thereof and the solvates thereof may be present in an amount ranging from 0.01% to 15% and for example from 0.05% to 10% by weight relative to the total weight of the composition.

The dye composition within the scope of the disclosure may further comprise at least one oxidation base. This at least one oxidation base may be chosen from the oxidation bases commonly used in oxidation dyeing, for example para-phenylenediamines, bis(phenyl)alkylenediamines, para-aminophenols, ortho-aminophenols and heterocyclic bases.

Examples of para-phenylenediamines that may be mentioned y include para-phenylenediamine, para-tolylenediamine, 2-chloro para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxy-ethyl)amino-2-chloroaniline, 2β-hydroxyethyl-para-phenylenediamine, 2-fluoro para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(3-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2β-hydroxyethyloxy-para-phenylenediamine, 2β-acetylaminoethyloxy-para-phenylenediamine, N-(β-methoxyethyl)-para-phenylenediamine, 4 aminophenylpyrrolidine, 2-thienyl-para-phenylenediamine and 2β-hydroxyethylamino-5-aminotoluene, and the acid-addition salts thereof.

Among the para-phenylenediamines described above, non-limiting mention can be made of para-phenylenediamine, para-tolylenediamine, 2-isopropyl-para-phenylenediamine, 2β-hydroxyethyl-para-phenylenediamine, 2β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2β-acetylaminoethyloxy-para-phenylenediamine, and the acid-addition salts thereof.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methyl-aminophenyl)tetramethylenediamine, N,N'-bis(ethyl)-N,N'-bis(4'-amino-3'-methylphenyl)ethylenediamine and 1,8-bis(2,5-diamino-phenoxy)-3,6-dioxaoctane, and the acid-addition salts thereof.

Among the para-aminophenols, examples that may be mentioned include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the acid-addition salts thereof.

Among the ortho-aminophenols, examples that may be mentioned include 2-aminophenol, 2-amino-5-methylphenol, 2-amino-6-methylphenol and 5-acetamido-2-aminophenol, and the acid-addition salts thereof.

Among the heterocyclic bases, examples that may be mentioned include pyridine derivatives, pyrimidine derivatives and pyrazole derivatives, and derivatives of pyrazolo[1,2a]pyrazol-1-one type.

Among the pyridine derivatives, non-limiting mention may be made of the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid-addition salts thereof.

Among the pyrimidine derivatives, non-limiting mention may be made, for example, of the compounds described in patents DE 2 359 399; JP 88-169 571; JP 05 163 124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR 2 750 048, and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-amino-pyrazolo[1,5-a]pyrimidin-7-yl)(2-hydroxyethyl)amino]ethanol, 2-[(7-amino-pyrazolo[1,5-a]pyrimidin-3-yl)(2-hydroxyethyl)amino]-ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethyl-pyrazolo[1,5-a]pyrimidine-3,7-diamine and 3-amino-5-methyl-7-imidazol-ylpropylaminopyrazolo[1,5-a]pyrimidine, and the acid-addition salts thereof and the tautomeric forms thereof, when a tautomeric equilibrium exists.

Among the pyrazole derivatives, non-limiting mention may be made of the compounds described in patents DE 3 843 892 and DE 4 133 957 and patent applications WO 94/08969, WO 94/08970, FR 2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl 3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino 3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino 1-methylpyrazole, and the acid-addition salts thereof.

Among the derivatives of pyrazolo[1,2a]pyrazol-1-one type, exemplary mention may be made of compounds such as 2,3-diamino-6,7-dihydro-1H,5H-pyrazolo[1,2a]pyrazol-1-one.

The dye composition within the scope of the disclosure may comprise at least one coupler commonly used for the dyeing of keratin fibers. Among these couplers, non-limiting mention may be made of meta-phenylenediamines, meta-aminophenols, meta-diphenols, naphthalene-based couplers and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine 3,5-diamino-2,6-dimethoxypyridine, 1N-(β-hydroxyethyl)amino-3,4-methylenedioxybenzene and 2,6-bis(β-hydroxyethylamino)toluene, and the acid-addition salts thereof.

In the dye composition that is within the scope of the disclosure, the at least one oxidation base can be present in an amount ranging from 0.001% to 10% and fro example from 0.005% to 6% by weight relative to the total weight of the composition. The at least one coupler can be present in an amount ranging from 0.001% to 10% and for example from 0.005% to 6% by weight relative to the total weight of the composition.

For example, the acids in the acid-addition salts of the oxidation bases and couplers are chosen from the hydrochlorides, hydrobromides, sulfates, citrates, succinates, tartrates, lactates, tosylates, benzenesulfonates, phosphates and acetates.

The dye composition within the scope of the disclosure may optionally further comprise at least one additional direct dye conventionally used for the dyeing of keratin fibers. This additional direct dye may be chosen from cationic and non-ionic species.

Non-limiting examples that may be mentioned include nitrobenzene dyes, azo, azomethine, methine, tetraazapentamethine, anthraquinone, naphthoquinone, benzoquinone, phenothiazine, indigoid, xanthine, phenanthridine and phthalocyanin dyes, triarylmethane-based dyes and natural dyes, alone or as mixtures.

It may be chosen, for example, from the following red or orange nitrobenzene dyes: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)-benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine, and 1-amino-2-nitro-4-hydroxy-5-methylbenzene.

The at least one additional direct dye may also be chosen from yellow and green-yellow nitrobenzene direct dyes. Examples that may be mentioned include the compounds chosen from: 1β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-(β-hydroxyethyl)amino-3-nitrochlorobenzene, 4(β-hydroxyethyl)amino-3-nitromethylbenzene, 4-(β,γ-dihydroxypropyl)amino-3-nitrotrifluoro-methylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl) methyl]amino-5-nitrobenzene, 1-(β-hydroxyethyl)amino-2-nitrobenzene and 4-(β-hydroxyethyl)amino-3-nitrobenzamide.

Non-limiting mention may also be made of blue or violet nitrobenzene direct dyes, for instance 1-(β-hydroxyethyl)amino-4-N,N-bis(β-hydroxyethyl)amino-2-nitrobenzene, 1-(γ-hydroxypropyl)amino-4-N,N-bis(β-hydroxyethyl) amino-2-nitrobenzene, 1-(β-hydroxyethyl)amino-4-(N-methyl-N-β-hydroxyethyl)amino-2-nitrobenzene, 1-(β-hydroxyethyl)amino-4-(N-ethyl-N-β-hydroxyethyl)amino-2-nitrobenzene, 1-(β,γ-dihydroxy-propyl)amino-4-(N-ethyl-N-β-hydroxyethyl)amino-2-nitrobenzene, and the 2-nitro-para-phenylenediamines of formula (III) below:

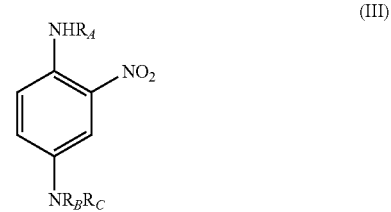

in which:

$R_B$ represents a $C_1$-$C_4$ alkyl, a β-hydroxyethyl, β-hydroxypropyl or γ-hydroxypropyl;

$R_A$ and $R_C$, which may be identical or different, represent a β-hydroxyethyl, β-hydroxypropyl, γ-hydroxypropyl or β,γ-dihydroxypropyl, wherein at least one of the radicals $R_B$, $R_C$ and $R_A$ represents a γ-hydroxypropyl, and $R_A$ and $R_C$ do not simultaneously represent β-hydroxyethyl when $R_B$ is a γ-hydroxypropyl radical, such as those described in FR 2 692 572.

Among the azo direct dyes that may be used according to the disclosure, exemplary mention may be made of the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369 and FR 2 844 269.

Among these compounds, mention may be made for instance, of the following dyes: 1,3-dimethyl-2-[[4-(dimethylamino)phenyl]azo]-1H-imidazolium chloride, 1,3-dimethyl-2-[(4-aminophenyl)azo]-1H-imidazolium chloride, 1-methyl-4-[(methylphenylhydrazono)methyl]-pyridinium methyl sulfate.

Among the azo direct dyes, non-limiting mention may also be made of the following dyes, described in the COLOUR INDEX INTERNATIONAL 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, and Disperse Black 9.

Non-limiting mention may also be made of 1-(4'-amino-diphenylazo)-2-methyl-4,4-bis(β-hydroxyethyl)aminobenzene and 4-hydroxy-3-(2-methoxyphenylazo)-1-naphthalenesulfonic acid.

Among the quinone direct dyes, non-limiting mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, and Basic Blue 99, and also the following compounds: 1-N-methylmorpholiniumpropylamino-4-hydroxyanthraquinone, 1-aminopropylamino-4-methylaminoanthraquinone, 1-aminopropylamino-anthraquinone, 5β-hydroxyethyl-1,4-diaminoanthraquinone, 2-aminoethylaminoanthraquinone, and 1,4-bis(β,γ-dihydroxypropylamino)anthraquinone.

Among the azine dyes, non-limiting mention may be made of the following compounds: Basic Blue 17, and Basic Red 2.

Among the triarylmethane dyes that may be used according to the disclosure, non-limiting mention may be made of the following compounds: Basic Green 1, Acid Blue 9, Basic Violet 3, Basic Violet 14, Basic Blue 7, Acid Violet 49, Basic Blue 26, and Acid Blue 7.

Among the indoamine dyes that may be used according to the disclosure, non-limiting mention may be made of the following compounds: 2β-hydroxyethlyamino-5-[bis(β-4'-hydroxyethyl)amino]anilino-1,4-benzoquinone, 2β-hydroxyethylamino-5-(2'-methoxy-4'-amino)anilino-1,4-benzoquinone, 3-N(2'-chloro-4'-hydroxy)phenylacetylamino-6-methoxy-1,4-benzoquinoneimine, 3-N(3'-chloro-4'-methylamino)phenylureido-6-methyl-1,4-benzoquinone imine, and 3-[4'-N-(ethyl,carbamylmethyl)amino]phenyl-ureido-6-methyl-1,4-benzoquinoneimine.

Among the dyes of tetraazapentamethine type that may be used according to the disclosure, non-limiting mention may be made of the following dyes: 2-((E)-{(E)-[(1,3-dimethyl-1,3-dihydro-2H-imidazol-2-ylidene)hydrazono] methyl}diazenyl)-1,3-dimethyl-1H-imidazol-3-ium chloride; 2-{(E)-[(1Z)-N-(1,3-dimethyl-1,3-dihydro-2H-imidazol-2-ylidene)ethanehydrazonoyl]diazenyl}-1,3-dimethyl-1H-imidazol-3-ium chloride; 4-methoxy-2-((E)-{(1E)-1-[(2E)-(4-methoxy-1-methylpyrid-2(1H)-ylidene) hydrazono]ethyl}diazenyl)-1-methylpyridinium chloride; 1-methyl-2-((E)-{(1E)-1-[(2E)-(1-methylpyrid-2(1H)-ylidene)hydrazono]ethyl}diazenyl)pyridinium chloride; 1-(2-hydroxyethyl)-2-[(E)-((1E)-1-{(2E)-[1-(2-hydroxyethyl)pyrid-2(1H)-ylidene]hydrazono}ethyl)diazenyl]pyridinium chloride; 1-methyl-2-((E)-{(E)-[(2Z)-(1-methylpyrid-2(1H)-ylidene)hydrazono]methyl}diazenyl)-pyridinium chloride; and 1-(2-hydroxyethyl)-2-[(E)-((E)-{(2E)-[1-(2-hydroxyethyl)pyrid-2(1H)-ylidene]hydrazono}methyl)diazenyl]pyridinium acetate.

Among the natural additional direct dyes that may be used according to the disclosure, non-limiting mention may be made of lawsone, juglone, alizarin, purpurin, carminic acid, kermesic acid, purpurogallin, protocatechaldehyde, indigo, isatin, curcumin, spinulosin and apigenidin. It is also possible to use extracts or decoctions comprising these natural dyes, and for example henna-based poultices or extracts.

The at least one additional direct dye may be present in the composition in an amount ranging from 0.001% to 20% and for example from 0.01% to 10% by weight relative to the total weight of the composition.

The medium that is suitable for dyeing, also known as the dye support, may comprise water or a mixture of water and of at least one organic solvent to dissolve the compounds that may not be sufficiently water-soluble.

For example, the at least one organic solvent is chosen from linear and branched, saturated, monoalcohols and diols, comprising from 2 to 10 carbon atoms, such as ethyl alcohol, isopropyl alcohol, hexylene glycol(2-ethyl-2,4-pentanediol), neopentyl glycol and 3-ethyl-1,5-pentanediol; aromatic alcohols such as benzyl alcohol and phenylethyl alcohol; glycols or glycol ethers, for instance ethylene glycol monomethyl, monoethyl or monobutyl ether, propylene glycol or ethers thereof, for instance propylene glycol monomethyl ether, butylene glycol and dipropylene glycol; and diethylene glycol alkyl ethers, such as $C_1$-$C_4$, for instance diethylene glycol monoethyl ether and monobutyl ether.

The solvents described above may represent from 1% to 40% by weight and for example from 5% to 30% by weight relative to the total weight of the composition.

The dye composition within the scope of the disclosure may also further comprise at least one adjuvant commonly used in dye compositions, such as anionic, cationic, nonionic, amphoteric and/or zwitterionic surfactants, anionic, cationic, nonionic, amphoteric and/or zwitterionic polymers, mineral and/or organic thickeners, and for example anionic, cationic, nonionic and/or amphoteric associative polymers, antioxidants, penetrants, sequestrants, fragrances, buffers, dispersants, conditioning agents, for instance volatile and/or non-volatile, modified and/or unmodified silicones, film-forming agents, ceramides, preserving agents, stabilizers and/or opacifiers.

The at least one adjuvant can be present in an amount ranging from 0.01% to 20% by weight relative to the total weight of the composition.

Needless to say, a person skilled in the art will take care to select this or these optional additional compound(s) such that the beneficial properties intrinsically associated with the dye composition within the scope of the disclosure are not, or are not substantially, adversely affected by the envisaged addition(s).

The pH of the dye composition according to the disclosure can range from 3 to 12 and for example from 5 to 11. It may be adjusted to the desired value via acidifying or basifying agents commonly used in the dyeing of keratin fibers, or alternatively using standard buffer systems. Modification of the pH within these ranges can promote the formation of the compounds of formula (I) and/or (II).

Among the acidifying agents, non-limiting examples that may be mentioned include mineral acids, for instance hydrochloric acid, nitric acid or sulfuric acid, or organic acids, for instance compounds comprising at least one carboxylic acid function, for instance acetic acid, tartaric acid, citric acid or lactic acid, a sulfonic acid function, a phosphonic acid function or a phosphoric acid function.

Among the basifying agents, non-limiting examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula (IV) below:

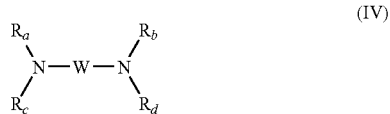

in which W is a propylene residue optionally substituted with a hydroxyl group or a $C_1$-$C_4$ alkyl; Ra, Rb, Rc and Rd, which may be identical or different, represent a hydrogen atom, a $C_1$-$C_4$ alkyl or a $C_1$-$C_4$ hydroxyalkyl.

The compounds of formula (II) may be obtained from the compounds of formula (I) by reaction with atmospheric oxygen or via the action of at least one oxidizing agent, which may be any oxidizing agent commonly used in the field. Thus, it may be chosen from hydrogen peroxide, urea peroxide, alkali metal bromates, persalts such as perborates and persulfates, and also enzymes, among which exemplary mention may be made of peroxidases, 2-electron oxidoreductases such as uricases, and 4-electron oxygenases, for instance laccases.

The oxidizing agent may also contribute to simultaneous lightening of keratin fibers (lightening dyeing) when the composition comprises oxidation bases or oxidation couplers.

The dye composition according to the disclosure may be in various forms, such as in the form of liquids, creams or gels, or in any other form that is suitable for dyeing keratin fibers, such as human hair.

The coloration obtained may depend on the compounds that are applied to the keratin fibers. The coloration can be more intense when all these compounds are in the form of dyes of azomethine type comprising a pyrazolopyridine unit, i.e. when they are of formula (II). By promoting the formation of the compounds of formula (I) from the compounds of formula (II), the intensity of the coloration may be reduced until it has disappeared.

Provided is also at least one compound chosen from the leuco form compounds of formula (I), the dyes of azomethine type comprising a pyrazolopyridine unit of formula (II) as defined previously, provided that when X is hydroxyl or V is oxygen, at least one Y is hydroxyl or a group $NR'_2R'_3$; and also the mesomeric forms, isomers and tautomers thereof, the acid-addition salts thereof and solvates thereof;

with the exception of the following compound:

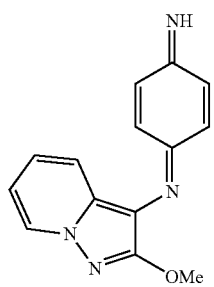

and also the mesomeric forms thereof, the acid-addition salts thereof and the solvates thereof.

The method for dyeing keratin fibers comprises applying to the keratin fibers at least one composition comprising at least one compound chosen from the leuco form compounds of formula (I), the dyes of azomethine type comprising a pyrazolopyridine unit of formula (II) as defined previously, and also the mesomeric forms, isomers and tautomers thereof, the acid-addition salts thereof and the solvates thereof.

According to at least one embodiment, the at least one composition comprises at least one compound chosen from the compounds of formulae (II), (IIa) and (IIb).

The at least one oxidizing agent may be present in the at least one composition. It may also be applied separately, as a pretreatment or a post-treatment.

The application of the at least one composition may or may not be followed by rinsing.

The leave-on time of the at least one composition can range from 3 to 60 minutes, such as from 5 to 40 minutes and further such as from 10 to 30 minutes.

The application temperature can be at room temperature, and also can be at a temperature ranging from 25 to 55° C.

Provided is also a multi-compartment device or kit for the dyeing of keratin fibers as described above.

The multi-compartment device comprises at least one first compartment comprising at least one compound chosen from compounds of formulae (I), and at least one second compartment comprising at least one oxidizing agent, and optionally at least one compound of formulae (II), and at least one alkaline agent.

This device may be equipped with an applicator for applying the desired mixture to the hair, such as the devices described in patent FR 2 586 913.

The examples that follow serve to illustrate the disclosure without, however, being limiting in scope.

EXAMPLES

Examples of Synthesis

Example 1

Synthesis of 2-({(3E)-4-amino-6-imino-3-[(2-methoxypyrazolo[1,5-a]pyrid-3-yl)imino]cyclohexa-1,4-dien-1-yl}oxy)ethanol

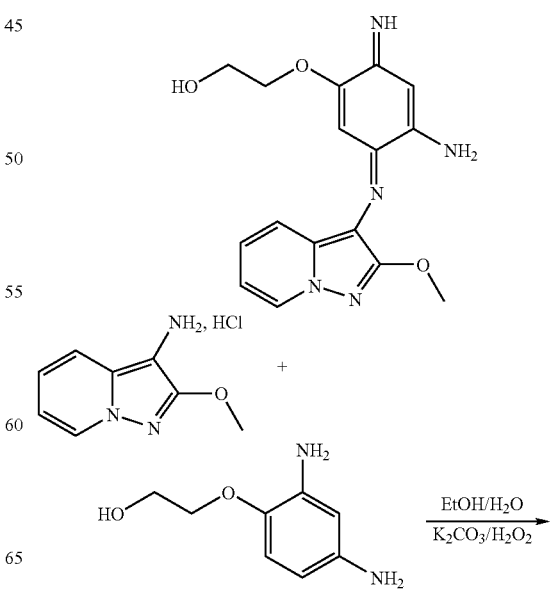

-continued

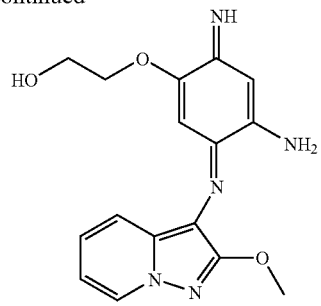

5 mmol of 2-methoxypyrazolo[1,5-a]pyrid-3-amine dihydrochloride dissolved in 20 ml of ethanol were placed in a 100 ml one-necked round-bottomed flask.

5 mmol of coupler 2-(2,4-diaminophenoxy)ethanol and a solution of 20 mmol of potassium carbonate in 3 ml of water were added to this solution.

100 microliters of 9-volumes aqueous hydrogen peroxide solution were then added and stirring was then continued for 24 hours at this temperature.

After diluting with 100 ml of water, the expected compound was isolated by filtration, washed with water and then dried under vacuum at 30° C. in the presence of a drying agent.

337 mg of expected product were thus isolated in the form of a dark brown powder.

Analysis by Mass Spectrometry

The quasi-molecular ion [M+H]+ of the expected molecule $C_{16}H_{17}N_5O_3$ was mainly detected.

Example 2

Synthesis of 2-[(3-{[(1E)-2-amino-5-(2-hydroxyethoxy)-4-iminocyclohexa-2,5-dien-1-ylidene]amino}pyrazolo[1,5-a]pyrid-2-yl)oxy]ethanol

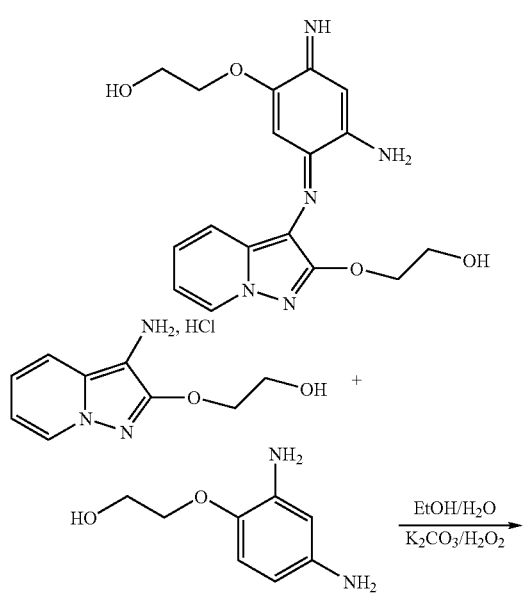

-continued

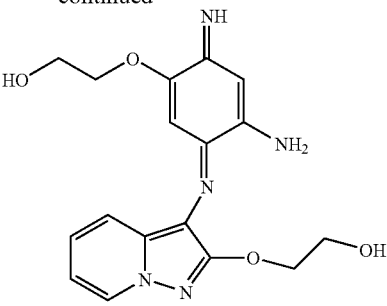

4.35 mmol of 2-[(3-aminopyrazolo[1,5-a]pyrid-2-yl)oxy]ethanol hydrochloride dissolved in 25 ml of ethanol were placed in a 100 ml one-necked round-bottomed flask.

4.35 mmol of coupler 2-(2,4-diaminophenoxy)ethanol and a solution of 17.41 mmol of potassium carbonate and 3 ml of water were added to this solution.

100 microliters of 20-volumes aqueous hydrogen peroxide solution were then added and stirring was then continued for 24 hours at this temperature.

After diluting with 100 ml of water, the expected compound was isolated by filtration, washed with water and then dried under vacuum at 30° C. in the presence of a drying agent.

The dark brown isolated product (392.6 mg) corresponded to the expected product.

Analysis by Mass Spectrometry

The quasi-molecular ion [M+H]+ of the expected molecule $C_{17}H_{19}N_5O_4$ was mainly detected.

Example 3

Synthesis of 2-({(3E)-4-amino-3-[(2-{[2-(dimethylamino)ethyl]amino}pyrazolo[1,5-a]pyrid-3-yl)imino]-6-iminocyclohexa-1,4-dien-1-yl}oxy)ethanol

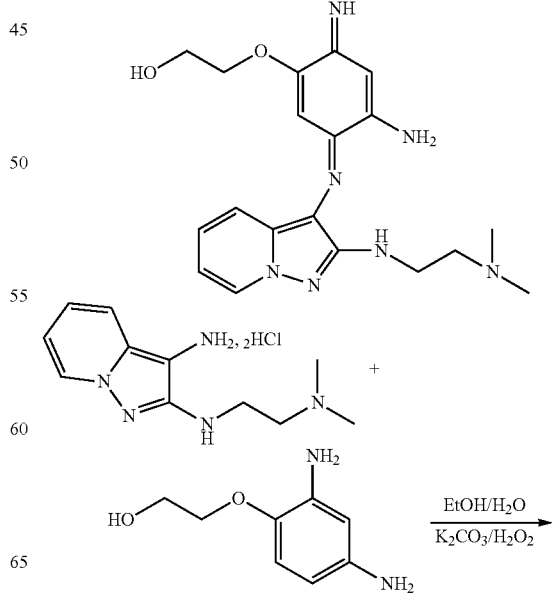

-continued

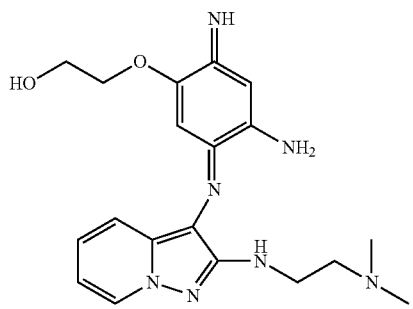

3.04 mmol of N2-[2-(dimethylamino)ethyl]pyrazolo[1,5-a]pyridine-2,3-diamine dihydrochloride dissolved in 25 ml of ethanol were placed in a 100 ml one-necked round-bottomed flask.

3.04 mmol of coupler 2-(2,4-diaminophenoxy)ethanol and a solution of 18.24 mmol of potassium carbonate and 3 ml of water were added to this solution.

100 microliters of 20-volumes aqueous hydrogen peroxide solution were then added and stirring was then continued for 24 hours at this temperature.

After diluting with 100 ml of water, the expected compound was isolated by filtration, washed with water and then dried under vacuum at 40° C. in the presence of a drying agent.

The expected product was thus isolated in the form of a dark brown solid (116.4 mg).

Analysis by Mass Spectrometry

The expected molecule $C_{19}H_{25}N_7O_2$ was mainly detected at m/z, ESP+=384 and 192.

Example 4

Synthesis of (4E)-4-{[2-(2-hydroxyethoxy)pyrazolo[1,5-a]pyrid-3-yl]imino}-5-[(2-hydroxyethyl)amino]-2-methylcyclohexa-2,5-dien-1-one

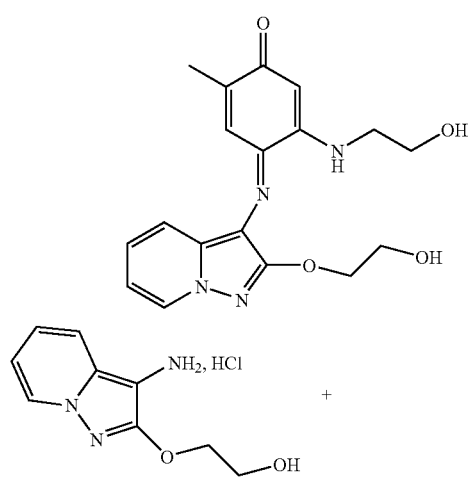

-continued

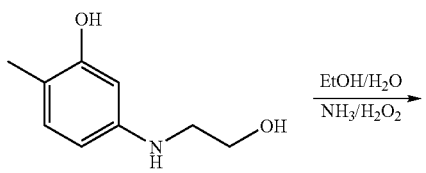

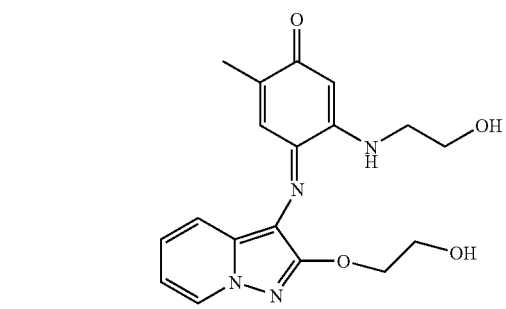

5 mmol of 2-[(3-aminopyrazolo[1,5-a]pyrid-2-yl)oxy]ethanol hydrochloride dissolved in 2 ml of ethanol and 8 ml of water were placed in a 100 ml one-necked round-bottomed flask.

5 mmol of coupler 5-[(2-hydroxyethyl)amino]-2-methylphenol, and 1 ml of 20% aqueous ammonia so as to obtain a pH of 9.5, and 1 ml of aqueous hydrogen peroxide solution as oxidizing agent were added to this solution.

The reaction medium (violet solution) was stirred for 30 minutes at room temperature, and the formation of the expected compound was monitored by LC/MS spectrometry.

Analysis by Mass Spectrometry

The expected molecule $C_{18}H_{20}N_4O_4$ was mainly detected.

Examples of Dyeing

Examples 1 and 2 of Dyeing in Acidic Medium

The following dye compositions were prepared:

| Dye Example | $10^{-3}$ mol |
|---|---|
| Dye support (1) | (*) |
| Demineralized water qs | 100 g |

Example 1

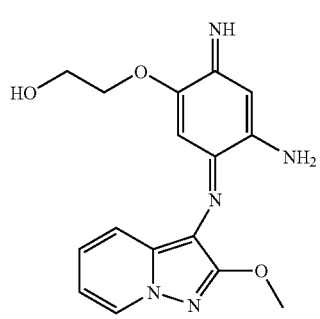

Example 2

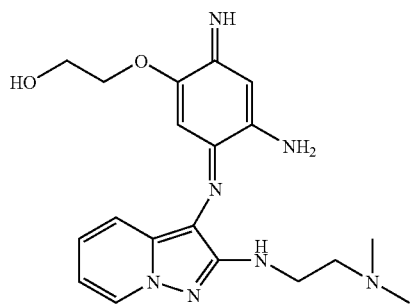

(*): dye support (1) pH 7
dye support (1) pH 7:

| | |
|---|---|
| 96° ethyl alcohol | 20.8 g |
| Pentasodium salt of diethylenetriaminepentaacetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

Each mixture obtained was applied to locks of grey hair containing 90% white hairs. After a leave-on time of 30 minutes, the locks were rinsed, washed with a standard shampoo, rinsed again and then dried.

The shades obtained were given in the table below:

| Example | 1 | 2 |
|---|---|---|
| Shade observed | Bright red | Bright blue |

For the colorations in oxidizing media: at the time of the use, each of the compositions described above was mixed with an equal weight of 20-volumes aqueous hydrogen peroxide solution (6% by weight). A final pH of 7 was obtained.

The shades obtained were given in the table below:

| Example | 1 | 2 |
|---|---|---|
| Shade observed | Bright red | Bright blue-green |

Examples 3 and 4 of Dyeing in Basic Medium

The following dye compositions were prepared:

| | |
|---|---|
| Dye Example | $10^{-3}$ mol |
| Dye support (2) | (*) |
| Demineralized water qs | 100 g |

Example 3

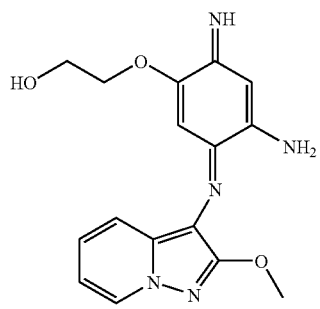

Example 4

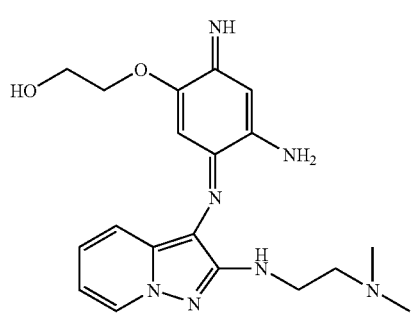

(*): dye support (2) pH 9.5
dye support (2): pH 9.5

| | |
|---|---|
| 96° ethyl alcohol | 20.8 g |
| Pentasodium salt of diethylenetriaminepentaacetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

Each mixture obtained was applied to locks of grey hair containing 90% white hairs. After a leave-on time of 30 minutes, the locks were rinsed, washed with a standard shampoo, rinsed again and then dried.

The shades obtained were given in the table below:

| Example | 3 | 4 |
|---|---|---|
| Shade observed | Bright red | Blue-green |

For the oxidizing media: at the time of use, each of the compositions described above was mixed with an equal weight of 20-volumes aqueous hydrogen peroxide solution (6% by weight). A final pH of 9.5 was obtained.

The shades obtained were given in the table below:

| Example | 3 | 4 |
|---|---|---|
| Shade observed | Bright red | Blue-green |

What is claimed is:
1. A method for dyeing keratin fibers comprising
applying to the keratin fibers at least one composition comprising at least one compound chosen from leuco form compounds of formula (I), dyes of azomethine type comprising a pyrazolopyridine unit of formula (II), mesomeric forms, isomers and tautomers thereof, acid-addition salts thereof, and solvates thereof:

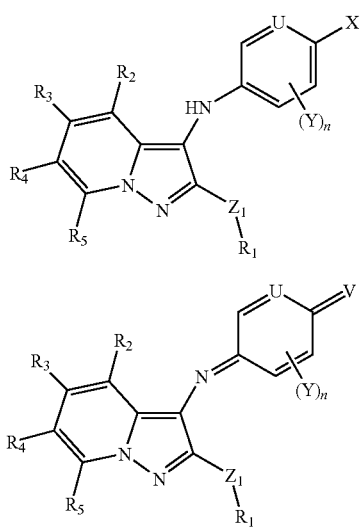

in which:

Z₁ represents an oxygen atom, or a group $NR_6$, when $Z_1$ represents $NR_6$ then $R_1$ and $R_6$ can form, together with the nitrogen atom to which they are attached, a saturated, unsaturated or aromatic, optionally substituted 5- to 8-membered heterocycle, $Z_1$ can also represent a divalent radical S, SO or $SO_2$ when $R_1$ is a methyl, $R_1$ and $R_6$ independently represent:
a hydrogen atom,
an optionally substituted $C_1$-$C_{10}$ alkyl radical, wherein the substituent can be a saturated, unsaturated or aromatic, optionally substituted 5- to 8-membered (hetero)cycle, or
a saturated, unsaturated or aromatic, optionally substituted 5- to 8-membered (hetero)cycle, $R_2$, $R_3$, $R_4$ and $R_5$ independently represent:
a hydrogen atom,
an optionally substituted $C_1$-$C_4$ alkyl,
a group chosen from $NH_2$, $NHR_{10}$, $NR_{11}R_{12}$, OH and $OR_9$, wherein $R_9$ and $R_{10}$ independently represent a linear or branched, optionally substituted $C_1$-$C_6$ alkyl, $R_{11}$ and $R_{12}$, which may be identical or different, represent an optionally substituted linear or branched $C_1$-$C_6$ alkyl, or $R_{11}$ and $R_{12}$, together with the nitrogen atom to which they are attached, form a saturated, unsaturated or aromatic 5- to 8-membered heterocycle optionally comprising at least one other radical chosen from N, O, S, $SO_2$ and CO, wherein the heterocycle is optionally substituted, or two adjacent $R_2$, $R_3$, $R_4$ and $R_5$, together with the two carbon atoms to which they are attached, form a saturated or unsaturated, optionally substituted (hetero)cycle;

n is an integer ranging from 0 to 3;

U represents CR or N;

R represents
a hydrogen atom,
a $C_1$-$C_4$ alkyl optionally substituted with a hydroxyl;
a $C_1$-$C_4$ alkoxy optionally substituted with a hydroxyl; or
a (di)($C_1$-$C_4$)alkylamino in which the alkyl part is optionally substituted with a hydroxyl;

X represents:
a hydroxyl; or
a group $NR'_1R''_1$, wherein $R'_1$ and $R''_1$ are independently chosen from a hydrogen atom; a $C_1$-$C_6$ alkyl radical optionally substituted with at least one radical chosen from a hydroxyl, ($C_1$-$C_2$)alkoxy, amino, and (di)($C_1$-$C_2$)alkylamino; a phenyl optionally substituted with at least one radical chosen from hydroxyl, amino, and ($C_1$-$C_2$)alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from oxygen and nitrogen atoms, and optionally substituted with at least one radical chosen from halogen atoms, aminos, (di)($C_1$-$C_4$) alkylamino, hydroxyl, carboxyl, carboxamido, ($C_1$-$C_2$) alkoxy, and $C_1$-$C_4$ alkyl radicals, optionally substituted with at least one radical chosen from hydroxyl, amino, (di)alkylamino, alkoxy, carboxyl, and sulfonyl;

when X represents a group $NHR'_1$ and when U represents a group CR in which R denotes an alkoxy, then X and U together can form a 6-membered ring of morpholine type, optionally substituted with at least one $C_1$-$C_4$ alkyl;

V represents
an oxygen atom; or
a group $NR'_1$, wherein $R'_1$ is chosen from a hydrogen atom; a $C_1$-$C_6$ alkyl optionally substituted with at least one radical chosen from hydroxyl, ($C_1$-$C_2$) alkoxy, amino and (di)($C_1$-$C_2$)alkylamino; a phenyl radical optionally substituted with at least one radical chosen from hydroxyl, amino and ($C_1$-$C_2$)alkoxy;

when V represents a group $NR'_1$ and when U represents a group CR in which R denotes an alkoxy, then V and U may form a 6-membered ring of morpholine type, optionally substituted with at least one $C_1$-$C_4$ alkyl;

Y, which may be identical or different, represent:
a hydroxyl;
a $C_1$-$C_4$ alkyl;
a $C_1$-$C_4$ hydroxyalkyl;
a halogen atom;
an oxygen atom substituted with a radical chosen from a $C_1$-$C_4$ alkyl, an aryl and a heteroaryl, these radicals optionally substituted with at least one hydroxyl; or
a group $NR'_2R'_3$;

$R'_2$ and $R'_3$, which may be identical or different, are chosen from
a hydrogen atom;
a $C_1$-$C_4$ alkylcarbonyl optionally substituted with a quaternary ammonium group, or with a cationic or non-cationic nitrogenous heterocycle optionally substituted with at least one $C_1$-$C_4$ alkyl;
an aminocarbonyl;
a $C_1$-$C_6$ alkyl optionally substituted with at least one radical chosen from hydroxyl, ($C_1$-$C_2$)alkoxy, amino, and (di)($C_1$-$C_2$)alkylamino; and
a phenyl radical optionally substituted with at least one radical chosen from hydroxyl, amino, and ($C_1$-$C_2$) alkoxy radicals; or $R'_2$ and $R'_3$ form, together with the nitrogen atom to which they are attached, a saturated or unsaturated, 5- to 7-membered heterocycle optionally comprising at least one additional heteroatom chosen from oxygen and nitrogen atom, and optionally substituted with at least one radical chosen from halogen atoms and amino, (di)($C_1$-$C_4$)alkylamino, hydroxyl, carboxyl, (di)alkylcarboxamido, ($C_1$-$C_2$)alkoxy, and $C_1$-$C_4$ alkyl, optionally substituted with at least one radical chosen from hydroxyl, amino, (di)alkylamino, alkoxy, carboxyl, and sulfonyl; or two radicals Y borne by two adjacent carbon atoms form, together with the carbon atoms to which they are attached, a saturated or unsaturated, aromatic or non-aromatic, 5- to 6-membered cyclic or heterocyclic group optionally substituted with at least one $C_1$-$C_4$ alkyl.

2. The method for dyeing keratin fibers according to claim 1, wherein Y represents a group $NR'_2R'_3$, in which $R'_2$ and $R'_3$, which may be identical or different, are chosen from a $C_1$-$C_4$ alkylcarbonyl optionally substituted with a quaternary ammonium group chosen from trialkylammonium, or with a cationic or non-cationic nitrogenous heterocycle chosen from imidazole, thiazole, pyridine, piperidine, pyrrolidine, pyrimidine, pyrazine, imidazolium, pyridinium, thiazolium, pyrrolidinium, piperidinium and pyrimidinium, optionally substituted with at least one $C_1$-$C_4$ alkyl.

3. The method for dyeing keratin fibers according to claim 1, wherein two radicals Y borne by two adjacent carbon atoms form, together with the carbon atoms to which they are attached, a saturated or unsaturated, aromatic or non-aromatic, 5- to 6-membered cyclic or heterocyclic group chosen from benzene, pyrrole, pyrrolidine, pyrazole, furan, pyrrolidine, morpholine or imidazole, optionally substituted with at least one $C_1$-$C_4$ alkyl.

4. The method for dyeing keratin fibers according to claim 1, in which $Z_1$ represents an oxygen atom, a radical $NR_6$ or a radical $NR_6$ which forms with $R_1$ a heterocycle.

5. The method for dyeing keratin fibers according to claim 4, in which $R_6$ is chosen from a hydrogen atom; a $C_1$-$C_6$ alkyl; a $C_1$-$C_6$ alkyl substituted with at least one radical chosen from a hydroxyl, an amino, a ($C_1$-$C_4$)alkylamino, and a di($C_1$-$C_4$)alkylamino; and a $C_1$-$C_6$ alkyl substituted with a nitrogenous heterocycle.

6. The method for dyeing keratin fibers according to claim 1, in which $R_1$ is chosen from a $C_1$-$C_6$ alkyl, a $C_1$-$C_6$ alkyl substituted with at least one hydroxyl, a $C_1$-$C_6$ alkyl substituted with at least one amino or at least one ($C_1$-$C_4$)alkylamino, and a $C_1$-$C_6$ alkyl substituted with at least one nitrogenous heterocycle.

7. The method for dyeing keratin fibers according to claim 1, in which $R_2$, $R_3$, $R_4$ and $R_5$ independently represent a hydrogen atom or a $C_1$-$C_4$ alkyl radical, or $R_4$ and $R_5$ together form a 5- to 8-membered ring.

8. The method for dyeing keratin fibers according to claim 1, in which U represents CR or N, and R represents a hydrogen atom, a $C_1$-$C_4$ alkyl, a $C_1$-$C_4$ alkoxy optionally substituted with at least one hydroxyl, or a (di)($C_1$-$C_4$)alkylamino in which the alkyl is optionally substituted with at least one hydroxyl.

9. The method for dyeing keratin fibers according to claim 1, in which X represents a hydroxyl; or a group $NR'_1R''_1$, wherein $R'_1$ and $R''_1$ are independently chosen from a hydrogen atom, and a $C_1$-$C_6$ alkyl optionally substituted with at least one hydroxyl, or $R'_1$ and $R''_1$, together with the nitrogen to which they are attached, form a heterocycle.

10. The method for dyeing keratin fibers according to claim 1, in which V represents an oxygen atom; a group $NR'_1$ in which $R'_1$ represents a hydrogen atom or a $C_1$-$C_6$ alkyl optionally substituted with at least one hydroxyl.

11. The method for dyeing keratin fibers according to claim 1, in which Y, which may be identical or different, represent a hydroxyl; a $C_1$-$C_4$ alkyl; a halogen atom; an oxygen atom substituted with a $C_1$-$C_4$ alkyl, which is optionally substituted with at least one hydroxyl; or a group $NR'_2R'_3$, wherein $R'_2$ and $R'_3$, which may be identical or different, are chosen from a hydrogen atom, a $C_1$-$C_4$ alkylcarbonyl, an aminocarbonyl, and a $C_1$-$C_6$ alkyl optionally substituted with at least one hydroxyl, or $R'_2$ and $R'_3$ form, together with the nitrogen atom to which they are attached, a saturated 5- to 7-membered heterocycle.

12. A composition for dyeing keratin fibers, comprising, in a suitable dyeing medium, at least one compound chosen from leuco form compounds of formula (I), dyes of azomethine type comprising a pyrazolopyridine unit of formula (II), mesomeric forms, isomers and tautomers thereof, acid-addition salts thereof, and solvates thereof,

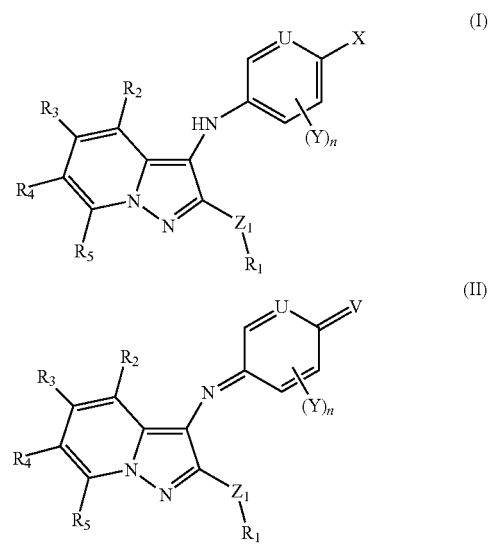

in which:

$Z_1$ represents an oxygen atom, or a group $NR_6$, when $Z_1$ represents $NR_6$ then $R_1$ and $R_6$ can form, together with the nitrogen atom to which they are attached, a saturated, unsaturated or aromatic, optionally substituted 5- to 8-membered heterocycle, $Z_1$ can also represent a divalent radical S, SO or $SO_2$ when $R_1$ is a methyl, $R_1$ and $R_6$ independently represent:

a hydrogen atom, an optionally substituted $C_1$-$C_{10}$ alkyl radical, wherein the substituent can be a saturated, unsaturated or aromatic, optionally substituted 5- to 8-membered (hetero)cycle, or a saturated, unsaturated or aromatic, optionally substituted 5- to 8-membered (hetero)cycle, $R_2$, $R_3$, $R_4$ and $R_5$ independently represent:

a hydrogen atom, an optionally substituted $C_1$-$C_4$ alkyl, a group chosen from $NH_2$, $NHR_{10}$, $NR_{11}R_{12}$, OH and $OR_9$, wherein $R_9$ and $R_{10}$ independently represent a linear or branched, optionally substituted $C_1$-$C_6$ alkyl, $R_{11}$ and $R_{12}$, which may be identical or different, represent an optionally substituted linear or branched $C_1$-$C_6$ alkyl, or $R_{11}$ and $R_{12}$, together with the nitrogen atom to which they are attached, form a saturated, unsaturated or aromatic 5- to 8-membered heterocycle optionally comprising at least one other radical chosen from N, O, S, $SO_2$ and CO, wherein the heterocycle is optionally substituted, or two adjacent $R_2$, $R_3$, $R_4$ and $R_5$, together with the two carbon atoms to which they are attached, form a saturated or unsaturated, optionally substituted (hetero)cycle;

n is an integer ranging from 0 to 3;

U represents CR or N;

R represents a hydrogen atom, a $C_1$-$C_4$ alkyl optionally substituted with a hydroxyl;

a $C_1$-$C_4$ alkoxy optionally substituted with a hydroxyl; or a (di)($C_1$-$C_4$)alkylamino in which the alkyl part is optionally substituted with a hydroxyl;

X represents:

a hydroxyl; or a group $NR'_1R''_1$, wherein $R'_1$ and $R''_1$ are independently chosen from a hydrogen atom; a $C_1$-$C_6$ alkyl radical optionally substituted with at least one radical chosen from a hydroxyl, ($C_1$-$C_2$)alkoxy, amino, and (di)($C_1$-$C_2$)alkylamino; a phenyl optionally substituted with at least one radical chosen from hydroxyl, amino, and ($C_1$-$C_2$)alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from oxygen and nitrogen atoms, and optionally substituted with at least one radical chosen from halogen atoms, aminos, (di)($C_1$-$C_4$)alkylamino, hydroxyl, carboxyl, carboxamido, ($C_1$-$C_2$)alkoxy, and $C_1$-$C_4$ alkyl radicals, optionally substituted with at least one radical chosen from hydroxyl, amino, (di)alkylamino, alkoxy, carboxyl, and sulfonyl;

when X represents a group $NHR'_1$ and when U represents a group CR in which R denotes an alkoxy, then X and U together can form a 6-membered ring of morpholine type, optionally substituted with at least one $C_1$-$C_4$ alkyl;

V represents an oxygen atom; or a group $NR'_1$, wherein $R'_1$ is chosen from a hydrogen atom; a $C_1$-$C_6$ alkyl optionally substituted with at least one radical chosen from hydroxyl, ($C_1$-$C_2$)alkoxy, amino and (di)($C_1$-$C_2$)alkylamino; a phenyl radical optionally substituted with at least one radical chosen from hydroxyl, amino and ($C_1$-$C_2$)alkoxy;

when V represents a group $NR'_1$ and when U represents a group CR in which R denotes an alkoxy, then V and U may form a 6-membered ring of morpholine type, optionally substituted with at least one $C_1$-$C_4$ alkyl;

Y, which may be identical or different, represent:

a hydroxyl;

a $C_1$-$C_4$ alkyl;

a $C_1$-$C_4$ hydroxyalkyl;

a halogen atom;

an oxygen atom substituted with a radical chosen from a $C_1$-$C_4$ alkyl, an aryl and a heteroaryl, these radicals optionally substituted with at least one hydroxyl; or a group $NR'_2R'_3$;

$R'_2$ and $R'_3$, which may be identical or different, are chosen from a hydrogen atom;

a $C_1$-$C_4$ alkylcarbonyl optionally substituted with a quaternary ammonium group, or with a cationic or non-cationic nitrogenous heterocycle optionally substituted with at least one $C_1$-$C_4$ alkyl;

an aminocarbonyl;

a $C_1$-$C_6$ alkyl optionally substituted with at least one radical chosen from hydroxyl, ($C_1$-$C_2$)alkoxy, amino, and (di)($C_1$-$C_2$)alkylamino; and a phenyl radical optionally substituted with at least one radical chosen from hydroxyl, amino, and ($C_1$-$C_2$) alkoxy radicals; or $R'_2$ and $R'_3$ form, together with the nitrogen atom to which they are attached, a saturated or unsaturated, 5- to 7-membered heterocycle optionally comprising at least one additional heteroatom chosen from oxygen and nitrogen atom, and optionally substituted with at least one radical chosen from halogen atoms and amino, (di)($C_1$-$C_4$)alkylamino, hydroxyl, carboxyl, (di)alkylcarboxamido, ($C_1$-$C_2$)alkoxy, and $C_1$-$C_4$ alkyl, optionally substituted with at least one radical chosen from hydroxyl, amino, (di)alkylamino, alkoxy, carboxyl, and sulfonyl; or two radicals Y borne by two adjacent carbon atoms form, together with the carbon atoms to which they are attached, a saturated or unsaturated, aromatic or non-aromatic, 5- to 6-membered cyclic or heterocyclic group optionally substituted with at least one $C_1$-$C_4$ alkyl, provided that when X is hydroxyl or V is oxygen, at least one Y is hydroxyl or a group $NR'_2R'_3$, with the exception of the following compound:

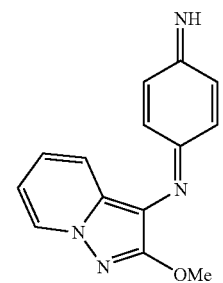

mesomeric forms thereof, isomers and tautomers thereof, acid-addition salts thereof, and solvates thereof.

13. The composition for dyeing keratin fibers according to claim 12, further comprising at least one oxidizing agent.

14. At least one compound chosen from leuco form compounds of formula (I) and dyes of azomethine type comprising a pyrazolopyridine unit of formula (II), mesomeric forms, isomers and tautomers thereof, acid-addition salts thereof and solvates thereof:

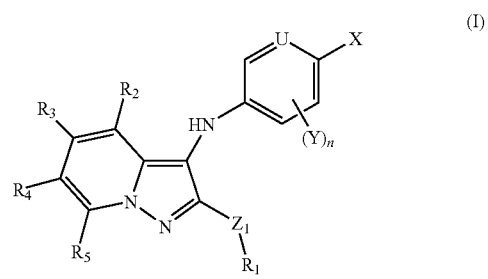

-continued

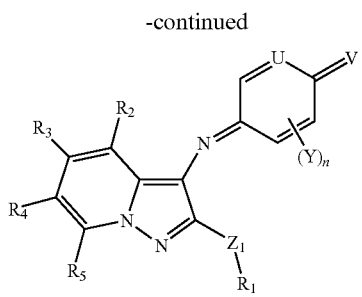

(II)

in which:
$Z_1$ represents an oxygen atom, or a group $NR_6$,
when $Z_1$ represents $NR_6$ then $R_1$ and $R_6$ can form, together with the nitrogen atom to which they are attached, a saturated, unsaturated or aromatic, optionally substituted 5- to 8-membered heterocycle,
$Z_1$ can also represent a divalent radical S, SO or $SO_2$ when $R_1$ is a methyl,
$R_1$ and $R_6$ independently represent:
a hydrogen atom,
an optionally substituted $C_1$-$C_{10}$ alkyl radical, wherein the substituent can be a saturated, unsaturated or aromatic, optionally substituted 5- to 8-membered (hetero)cycle, or
a saturated, unsaturated or aromatic, optionally substituted 5- to 8-membered (hetero)cycle,
$R_2$, $R_3$, $R_4$ and $R_5$ independently represent:
a hydrogen atom,
an optionally substituted $C_1$-$C_4$ alkyl,
a group chosen from $NH_2$, $NHR_{10}$, $NR_{11}R_{12}$, OH and $OR_9$, wherein
$R_9$ and $R_{10}$ independently represent a linear or branched, optionally substituted $C_1$-$C_6$ alkyl,
$R_{11}$ and $R_{12}$, which may be identical or different, represent an optionally substituted linear or branched $C_1$-$C_6$ alkyl, or $R_{11}$ and $R_{12}$, together with the nitrogen atom to which they are attached, form a saturated, unsaturated or aromatic 5- to 8-membered heterocycle optionally comprising at least one other radical chosen from N, O, S, $SO_2$ and CO, wherein the heterocycle is optionally substituted, or
two adjacent $R_2$, $R_3$, $R_4$ and $R_5$, together with the two carbon atoms to which they are attached, form a saturated or unsaturated, optionally substituted (hetero)cycle;
n is an integer ranging from 0 to 3;
U represents CR or N;
R represents
a hydrogen atom,
a $C_1$-$C_4$ alkyl optionally substituted with a hydroxyl;
a $C_1$-$C_4$ alkoxy optionally substituted with a hydroxyl; or
a (di)($C_1$-$C_4$)alkylamino in which the alkyl part is optionally substituted with a hydroxyl;
X represents:
a hydroxyl; or
a group $NR'_1R''_1$, wherein $R'_1$ and $R''_1$ are independently chosen from a hydrogen atom; a $C_1$-$C_6$ alkyl radical optionally substituted with at least one radical chosen from a hydroxyl, ($C_1$-$C_2$)alkoxy, amino, and (di)($C_1$-$C_2$)alkylamino; a phenyl optionally substituted with at least one radical chosen from hydroxyl, amino, and ($C_1$-$C_2$)alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from oxygen and nitrogen atoms, and optionally substituted with at least one radical chosen from halogen atoms, aminos, (di)($C_1$-$C_4$) alkylamino, hydroxyl, carboxyl, carboxamido, ($C_1$-$C_2$) alkoxy, and $C_1$-$C_4$ alkyl radicals, optionally substituted with at least one radical chosen from hydroxyl, amino, (di)alkylamino, alkoxy, carboxyl, and sulfonyl;
when X represents a group $NHR'_1$ and when U represents a group CR in which R denotes an alkoxy, then X and U together can form a 6-membered ring of morpholine type, optionally substituted with at least one $C_1$-$C_4$ alkyl;
V represents
an oxygen atom; or
a group $NR'_1$, wherein $R'_1$ is chosen from a hydrogen atom; a $C_1$-$C_6$ alkyl optionally substituted with at least one radical chosen from hydroxyl, ($C_1$-$C_2$) alkoxy, amino and (di)($C_1$-$C_2$)alkylamino; a phenyl radical optionally substituted with at least one radical chosen from hydroxyl, amino and ($C_1$-$C_2$)alkoxy;
when V represents a group $NR'_1$ and when U represents a group CR in which R denotes an alkoxy, then V and U may form a 6-membered ring of morpholine type, optionally substituted with at least one $C_1$-$C_4$ alkyl;
Y, which may be identical or different, represent:
a hydroxyl;
a $C_1$-$C_4$ alkyl;
a $C_1$-$C_4$ hydroxyalkyl;
a halogen atom;
an oxygen atom substituted with a radical chosen from a $C_1$-$C_4$ alkyl, an aryl and a heteroaryl, these radicals optionally substituted with at least one hydroxyl; or
a group $NR'_2R'_3$;
$R'_2$ and $R'_3$, which may be identical or different, are chosen from
a hydrogen atom;
a $C_1$-$C_4$ alkylcarbonyl optionally substituted with a quaternary ammonium group, or with a cationic or non-cationic nitrogenous heterocycle optionally substituted with at least one $C_1$-$C_4$ alkyl;
an aminocarbonyl;
a $C_1$-$C_6$ alkyl optionally substituted with at least one radical chosen from hydroxyl, ($C_1$-$C_2$)alkoxy, amino, and (di)($C_1$-$C_2$)alkylamino; and
a phenyl radical optionally substituted with at least one radical chosen from hydroxyl, amino, and ($C_1$-$C_2$) alkoxy radicals; or
$R'_2$ and $R'_3$ form, together with the nitrogen atom to which they are attached, a saturated or unsaturated, 5- to 7-membered heterocycle optionally comprising at least one additional heteroatom chosen from oxygen and nitrogen atom, and optionally substituted with at least one radical chosen from halogen atoms and amino, (di) ($C_1$-$C_4$)alkylamino, hydroxyl, carboxyl, (di)alkylcarboxamido, ($C_1$-$C_2$)alkoxy, and $C_1$-$C_4$ alkyl, optionally substituted with at least one radical chosen from hydroxyl, amino, (di)alkylamino, alkoxy, carboxyl, and sulfonyl; or
two radicals Y borne by two adjacent carbon atoms form, together with the carbon atoms to which they are attached, a saturated or unsaturated, aromatic or non-aromatic, 5- to 6-membered cyclic or heterocyclic group optionally substituted with at least one $C_1$-$C_4$ alkyl, provided that when X is hydroxyl or V is oxygen, at least one Y is hydroxyl or a group $NR'_2R'_3$, with the exception of the following compound:

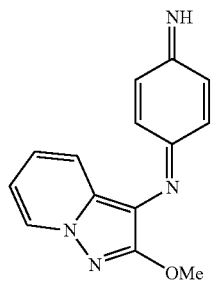

and mesomeric forms thereof, acid-addition salts thereof and solvates thereof.

15. A multi-compartment dyeing kit, comprising at least one first compartment which comprises at least one compound of formula (I), and at least one second compartment which comprises at least one oxidizing agent and optionally at least one compound of formula (II), and at least one alkaline agent;

wherein the at least one compound of formula (I), and the at least one compound of formula (II) are chosen from

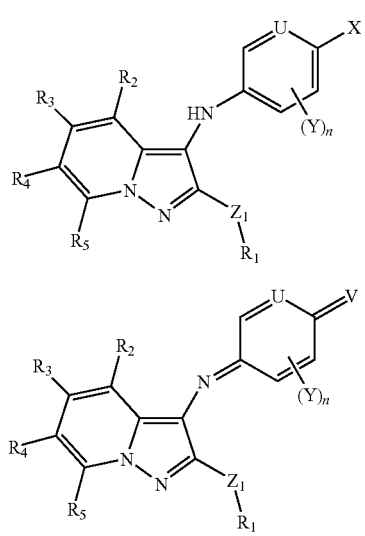

in which:

$Z_1$ represents an oxygen atom, or a group $NR_6$, when $Z_1$ represents $NR_6$ then $R_1$ and $R_6$ can form, together with the nitrogen atom to which they are attached, a saturated, unsaturated or aromatic, optionally substituted 5- to 8-membered heterocycle, $Z_1$ can also represent a divalent radical S, SO or $SO_2$ when $R_1$ is a methyl, $R_1$ and $R_6$ independently represent:

a hydrogen atom, an optionally substituted $C_1$-$C_{10}$ alkyl radical, wherein the substituent can be a saturated, unsaturated or aromatic, optionally substituted 5- to 8-membered (hetero)cycle, or a saturated, unsaturated or aromatic, optionally substituted 5- to 8-membered (hetero)cycle, $R_2$, $R_3$, $R_4$ and $R_5$ independently represent:

a hydrogen atom, an optionally substituted $C_1$-$C_4$ alkyl, a group chosen from $NH_2$, $NHR_{10}$, $NR_{11}R_{12}$, OH and $OR_9$, wherein $R_9$ and $R_{10}$ independently represent a linear or branched, optionally substituted $C_1$-$C_6$ alkyl, $R_{11}$ and $R_{12}$, which may be identical or different, represent an optionally substituted linear or branched $C_1$-$C_6$ alkyl, or $R_{11}$ and $R_{12}$, together with the nitrogen atom to which they are attached, form a saturated, unsaturated or aromatic 5- to 8-membered heterocycle optionally comprising at least one other radical chosen from N, O, S, $SO_2$ and CO, wherein the heterocycle is optionally substituted, or two adjacent $R_2$, $R_3$, $R_4$ and $R_5$, together with the two carbon atoms to which they are attached, form a saturated or unsaturated, optionally substituted (hetero)cycle;

n is an integer ranging from 0 to 3;

U represents CR or N;

R represents a hydrogen atom, a $C_1$-$C_4$ alkyl optionally substituted with a hydroxyl;

a $C_1$-$C_4$ alkoxy optionally substituted with a hydroxyl; or a (di)($C_1$-$C_4$)alkylamino in which the alkyl part is optionally substituted with a hydroxyl;

X represents:

a hydroxyl; or a group $NR'_1R''_1$, wherein $R'_1$ and $R''_1$ are independently chosen from a hydrogen atom; a $C_1$-$C_6$ alkyl radical optionally substituted with at least one radical chosen from a hydroxyl, ($C_1$-$C_2$)alkoxy, amino, and (di)($C_1$-$C_2$)alkylamino; a phenyl optionally substituted with at least one radical chosen from hydroxyl, amino, and ($C_1$-$C_2$)alkoxy;

when $R'_1$ and $R''_1$ are other than a hydrogen, $R'_1$ and $R''_1$ can form, together with the nitrogen atom to which they are attached, a saturated or unsaturated 5- to 7-membered heterocycle optionally comprising at least one additional heteroatom chosen from oxygen and nitrogen atoms, and optionally substituted with at least one radical chosen from halogen atoms, aminos, (di)($C_1$-$C_4$)alkylamino, hydroxyl, carboxyl, carboxamido, ($C_1$-$C_2$)alkoxy, and $C_1$-$C_4$ alkyl radicals, optionally substituted with at least one radical chosen from hydroxyl, amino, (di)alkylamino, alkoxy, carboxyl, and sulfonyl;

when X represents a group $NHR'_1$ and when U represents a group CR in which R denotes an alkoxy, then X and U together can form a 6-membered ring of morpholine type, optionally substituted with at least one $C_1$-$C_4$ alkyl;

V represents oxygen atom; or group $NR'_1$, wherein $R'_1$ is chosen from a hydrogen atom; a $C_1$-$C_6$ alkyl optionally substituted with at least one radical chosen from hydroxyl, ($C_1$-$C_2$)alkoxy, amino and (di)($C_1$-$C_2$)alkylamino; a phenyl radical optionally substituted with at least one radical chosen from hydroxyl, amino and ($C_1$-$C_2$)alkoxy;

when V represents a group $NR'_1$ and when U represents a group CR in which R denotes an alkoxy, then V and U may form a 6-membered ring of morpholine type, optionally substituted with at least one $C_1$-$C_4$ alkyl;

Y, which may be identical or different, represent:
- a hydroxyl;
- a $C_1$-$C_4$ alkyl;
- a $C_1$-$C_4$ hydroxyalkyl;
- a halogen atom;
- an oxygen atom substituted with a radical chosen from a $C_1$-$C_4$ alkyl, an aryl and a heteroaryl, these radicals optionally substituted with at least one hydroxyl; or
- a group $NR'_2R'_3$;

$R'_2$ and $R'_3$, which may be identical or different, are chosen from
- a hydrogen atom;
- a $C_1$-$C_4$ alkylcarbonyl optionally substituted with a quaternary ammonium group, or with a cationic or non-cationic nitrogenous heterocycle optionally substituted with at least one $C_1$-$C_4$ alkyl;
- an aminocarbonyl;
- a $C_1$-$C_6$ alkyl optionally substituted with at least one radical chosen from hydroxyl, $(C_1$-$C_2)$alkoxy, amino, and $(di)(C_1$-$C_2)$alkylamino; and
- a phenyl radical optionally substituted with at least one radical chosen from hydroxyl, amino, and $(C_1$-$C_2)$ alkoxy radicals; or $R'_2$ and $R'_3$ form, together with the nitrogen atom to which they are attached, a saturated or unsaturated, 5- to 7-membered heterocycle optionally comprising at least one additional heteroatom chosen from oxygen and nitrogen atom, and optionally substituted with at least one radical chosen from halogen atoms and amino, (di)$(C_1$-$C_4)$alkylamino, hydroxyl, carboxyl, (di)alkylcarboxamido, $(C_1$-$C_2)$alkoxy, and $C_1$-$C_4$ alkyl, optionally substituted with at least one radical chosen from hydroxyl, amino, (di)alkylamino, alkoxy, carboxyl, and sulfonyl; or two radicals Y borne by two adjacent carbon atoms form, together with the carbon atoms to which they are attached, a saturated or unsaturated, aromatic or non-aromatic, 5- to 6-membered cyclic or heterocyclic group optionally substituted with at least one $C_1$-$C_4$ alkyl.

\* \* \* \* \*

UNITED STATES PATENT AND TRADEMARK OFFICE
CERTIFICATE OF CORRECTION

| | | |
|---|---|---|
| PATENT NO. | : 7,892,294 B2 | |
| APPLICATION NO. | : 12/769140 | |
| DATED | : February 22, 2011 | |
| INVENTOR(S) | : Aziz Fadli et al. | |

It is certified that error appears in the above-identified patent and that said Letters Patent is hereby corrected as shown below:

On the Title page, item 73 (assignee), "L'oreal" should read -- L'Oreal --.

Claim 1, col. 66, line 11, "a phenyloptionally substituted" should read -- phenyl radical optionally substituted --.

Claim 12, col. 69, line 23, "a phenyloptionally substituted" should read -- phenyl radical optionally substituted --.

Claim 14, col. 71, line 65, "a phenyloptionally substituted" should read -- phenyl radical optionally substituted --.

Claim 14, col. 72, line 39, "R'2 and R'$_3$" should read -- R'$_2$ and R'$_3$ --.

Claim 15, col. 74, line 37, "a phenyloptionally substituted" should read -- phenyl radical optionally substituted --.

Signed and Sealed this
Twenty-sixth Day of April, 2011

David J. Kappos
*Director of the United States Patent and Trademark Office*